United States Patent
Zatopek et al.

(10) Patent No.: US 11,713,484 B2
(45) Date of Patent: Aug. 1, 2023

(54) MAPPING THE LOCATION, TYPE AND STRAND OF DAMAGED AND/OR MISMATCHED NUCLEOTIDES IN DOUBLE-STRANDED DNA

(71) Applicant: New England Biolabs, Inc., Ipswich, MA (US)

(72) Inventors: Kelly M. Zatopek, Wilmington, MA (US); Vladimir Potapov, Auburndale, MA (US); Jennifer Ong, Salem, MA (US); Laurence Ettwiller, Beverly, MA (US); Lixin Chen, Beverly, MA (US); Thomas C. Evans, Jr., Topsfield, MA (US); Andrew F. Gardner, Manchester, MA (US)

(*) Notice: Subject to any disclaimer, the term of this patent is extended or adjusted under 35 U.S.C. 154(b) by 289 days.

(21) Appl. No.: 16/758,190

(22) PCT Filed: Aug. 21, 2018

(86) PCT No.: PCT/US2018/047140
§ 371 (c)(1),
(2) Date: Apr. 22, 2020

(87) PCT Pub. No.: WO2019/099081
PCT Pub. Date: May 23, 2019

(65) Prior Publication Data
US 2020/0325533 A1 Oct. 15, 2020

Related U.S. Application Data

(60) Provisional application No. 62/586,932, filed on Nov. 16, 2017.

(51) Int. Cl.
*C12Q 1/6869* (2018.01)
*C12Q 1/6806* (2018.01)

(52) U.S. Cl.
CPC ......... *C12Q 1/6869* (2013.01); *C12Q 1/6806* (2013.01); *C12Q 2521/101* (2013.01); *C12Q 2521/307* (2013.01); *C12Q 2521/501* (2013.01); *C12Q 2521/514* (2013.01); *C12Q 2525/117* (2013.01)

(58) Field of Classification Search
None
See application file for complete search history.

(56) References Cited

U.S. PATENT DOCUMENTS

| | | | |
|---|---|---|---|
| 5,795,782 A | 8/1998 | Church et al. | |
| 6,015,714 A | 1/2000 | Baldarelli et al. | |
| 6,191,267 B1 | 2/2001 | Kong et al. | |
| 6,627,067 B1 | 9/2003 | Branton et al. | |
| 7,011,966 B2 | 3/2006 | Samuelson et al. | |
| 7,081,358 B2 | 7/2006 | Heiter et al. | |
| 7,238,485 B2 | 7/2007 | Akeson et al. | |
| 7,258,838 B2 | 8/2007 | Li et al. | |
| 7,820,424 B2 | 10/2010 | Xu et al. | |
| 7,943,303 B2 | 5/2011 | Xu et al. | |
| 8,158,388 B2 | 4/2012 | Evans et al. | |
| 8,163,529 B2 | 4/2012 | Xu et al. | |
| 8,592,150 B2* | 11/2013 | Drmanac | C12P 19/34 |
| | | | 435/6.12 |
| 9,951,327 B1* | 4/2018 | Rose | C12N 9/16 |
| 2004/0023207 A1* | 2/2004 | Polansky | A61K 48/005 |
| | | | 435/456 |
| 2005/0136462 A1 | 6/2005 | Zhu et al. | |
| 2006/0003171 A1 | 1/2006 | Igawa et al. | |
| 2009/0029477 A1 | 1/2009 | Meller et al. | |
| 2009/0123913 A1* | 5/2009 | Barany | B82Y 5/00 |
| | | | 435/6.14 |
| 2010/0009411 A1* | 1/2010 | Nelson | C12N 9/93 |
| | | | 435/89 |
| 2017/0298415 A1* | 10/2017 | Heller | C12Q 1/6806 |

FOREIGN PATENT DOCUMENTS

| | | |
|---|---|---|
| WO | 2002101095 A1 | 12/2002 |
| WO | 2006047183 A2 | 5/2006 |
| WO | 2009052366 A1 | 4/2009 |
| WO | 2014123822 A1 | 8/2014 |
| WO | 2015126840 A1 | 8/2015 |
| WO | 2015134785 A1 | 9/2015 |

OTHER PUBLICATIONS

Ramsay et al. CyDNA: Synthesis and Replication of Highly Cy-Dye Substituted DNA by an Evolved Polymerase. Journal of the American Chemical Society 132:5096-5104. (Year: 2010).*
Friedberg, Nature 421, 436-440 (2003).
Roos, et al. Trends Mol Med 12, 440-450 (2006).
Schumacher, et al. Trends Genet 24, 77-85 (2008).
O'Driscoll, Cold Spring Harb Perspect Biol 4 (2012).
Kubo, et al. Biochemistry 31, 3703-3708 (1992).
Collins, Mol Biotechnol 26, 249-261 (2004).
Sloan, et al., Trends Biotechnol (2018).
Hu, et al. Genes Dev 29, 948-960 (2015).
Koh, et al. Nat. Methods 12, 251-257 (2014).
Clark, et al. Genome Integr. 2, 10 (2011).
Bellamy, et al. J. Mol. Biol. 2005 345, 641-653.
(Continued)

*Primary Examiner* — Samuel C Woolwine
(74) *Attorney, Agent, or Firm* — New England Biolabs, Inc

(57) ABSTRACT

Providing herein, among other things, is a method comprising incubating a double-stranded nucleic acid having a nick with a nick translating activity, a ligase, and a nucleotide mix comprising at least one modified nucleotide, to generate a product comprising a patch of a newly synthesized strand of a duplex nucleic acid containing a plurality of modified nucleoside monophosphates that are at or adjacent to the site of the nick. In some embodiments, the method may be used to map damaged nucleoside monophosphates in a nucleic acid. Compositions and kits for use in performing the method are also provided.

34 Claims, 12 Drawing Sheets

Specification includes a Sequence Listing.

(56) References Cited

OTHER PUBLICATIONS

Heiter, et al., J. Mol. Biol. 2005 348, 631-640.
Xu, et al., Proc. Natl. Acad. Sci. USA 2001 98, 12990-12995.
Samuelson, et al., Nucl. Acids Res. 2004 32, 3661-3671.
Zhu, et al., J. Mol. Biol. 2004 337, 573-583.
Morgan, et al., Biol. Chem. 2000 381, 1123-1125.
Chan, Nucl. Acids Res. 2004 32, 6187-6199.
Sasnauskas, Proc. Natl. Acad. Sci. USA 2003 100, 6410-6415.
Jo, et al., PNAS 2007 104:2673-2678.
Xiao, et al., Nucleic Acids Res. 2007 35:e16.
Hsu, et al., Nature Biotechnology, 31: 827-832 (2013).
Soni, et al. Clin Chem 53:1996-2001 (2007).
Wescoe, et al., J Am Chem Soc 136, 16582-16587,2014.
Mohamad et al. Biotechnol Equip. Mar 4; 29(2): 205-220 (2015).
Paget, et al. FEMS Microbiology Letters, vol. 97, Issue 1-2, 1, 31-39 (1992).
Ensafi, et al. J. Mater. Chem.B, vol. 2, p. 3022 (2014).
Kohara, et al. Nucleic Acids Res 13, 6847-6866 (1985).
Fang et al. Mol Cell 4, 541-553 (1999).
McElhinny, et al. Proc Natl Acad Sci USA 107, 4949-4954 (2010).
Yao, et al. Proc Natl Acad Sci 110, 12942-12947 (2013).
Heider, et al. J. Biol Chem 292, 8835-8845 (2017).
Lipkin, et al. J Am Chem Soc 76, 2871-2872 (1954).
Li, et al. J. Am. Chem. Soc. 121, 5364-5372 (1999).
Tikh, et al. Biology Methods and Protocols 1, bpw004 (2016).
Sao, et al. Bioinformatics 23, 1866-1867 (2007).
Schreiber, et al. Proc Natl Acad Sci USA 110, 18910-18915 (2013).

\* cited by examiner

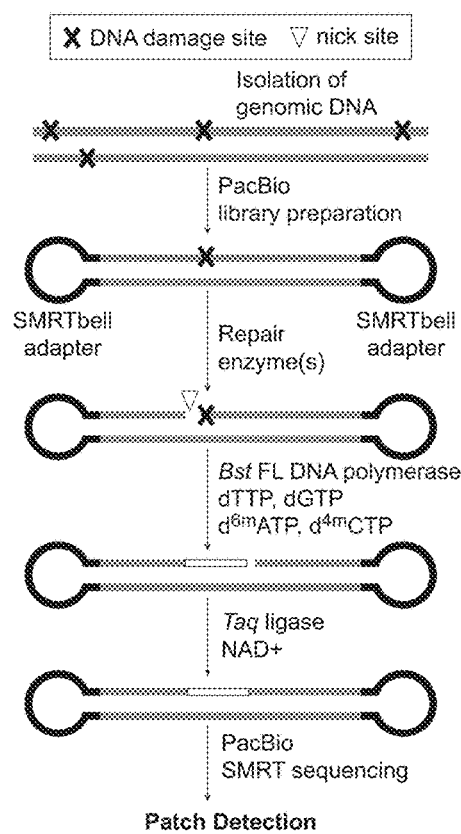
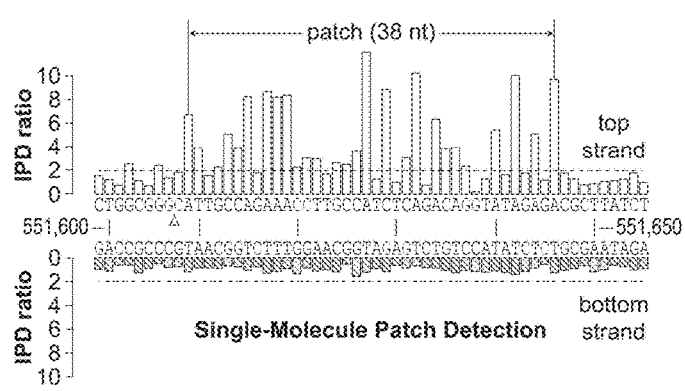
FIG. 3A
FIG. 3B

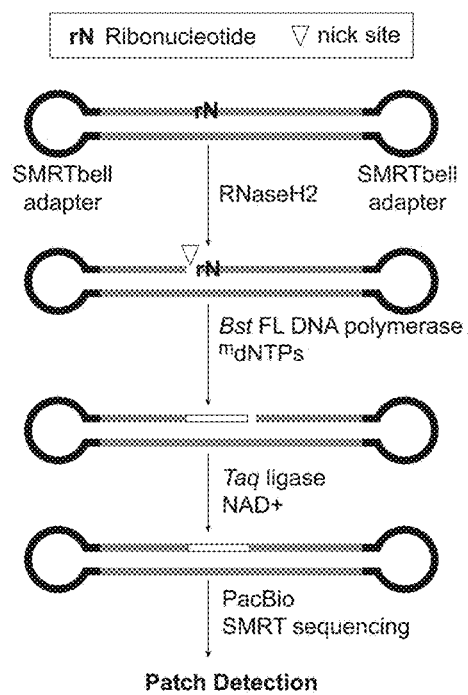 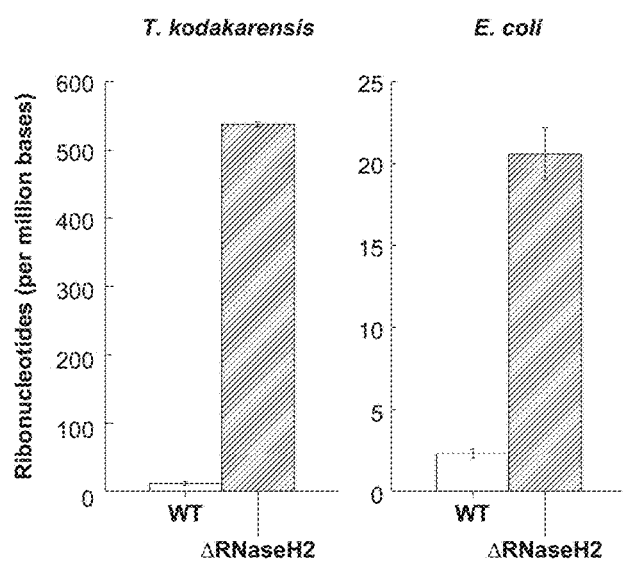
FIG. 4A
FIG. 4B

SEQUENCE LISTING

<160> NUMBER OF SEQ ID NOS: 6

<210> SEQ ID NO 1
<211> LENGTH: 44
<212> TYPE: DNA
<213> ORGANISM: artificial sequence
<220> FEATURE:
<223> OTHER INFORMATION: synthetic oligonucleotide

<400> SEQUENCE: 1
gagtcgatcg aatcgatcga tcgatcgatc gatcgatcga tgat        44

<210> SEQ ID NO 2
<211> LENGTH: 44
<212> TYPE: DNA
<213> ORGANISM: artificial sequence
<220> FEATURE:
<223> OTHER INFORMATION: synthetic oligonucleotide

<400> SEQUENCE: 2
atcatcgatc gatcgatcga tcgatcgatc gattcgatcg actc        44

<210> SEQ ID NO 3
<211> LENGTH: 56
<212> TYPE: DNA
<213> ORGANISM: artificial sequence
<220> FEATURE:
<223> OTHER INFORMATION: synthetic oligonucleotide

<400> SEQUENCE: 3
ctggcgggca ttgccagaaa ccttgccatc tcagacaggt atagagacgc ttatct        56

<210> SEQ ID NO 4
<211> LENGTH: 56
<212> TYPE: DNA
<213> ORGANISM: artificial sequence
<220> FEATURE:
<223> OTHER INFORMATION: synthetic oligonucleotide

<400> SEQUENCE: 4
agataagcgt ctctatacct gtctgagatg gcaaggtttc tggcaatgcc cgccag        56

<210> SEQ ID NO 5
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 5
ggcattgcca gaaaccttgc        20

<210> SEQ ID NO 6

```
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 6
gcaaggtttc tggcaatgcc                                              20
```

MAPPING THE LOCATION, TYPE AND STRAND OF DAMAGED AND/OR MISMATCHED NUCLEOTIDES IN DOUBLE-STRANDED DNA

CROSS REFERENCE

This application is a § 371 application of International Application No. PCT/US2018/047140, filed Aug. 21, 2018, which claims the benefit of U.S. Provisional Application No. 62/586,932, filed Nov. 16, 2017. The entire contents of these applications are incorporated herein by reference in their entirety.

SEQUENCE LISTING STATEMENT

This disclosure includes a Sequence Listing submitted electronically in ascii format under the file name "NEB-404-PUS_Seqence_Listing_Replacement.txt" created Apr. 25, 2022, with a file size of 1,525 bytes.

BACKGROUND

DNA is constantly under attack from both physiological metabolic processes and environmental agents, leading to DNA damage in vivo. DNA damage can result in mutagenesis, replication stalling and genome instability. Consequently, cells have evolved numerous mechanisms to repair DNA damage and maintain genome integrity (Friedberg, Nature 421, 436-440 (2003)). Determining the identities and frequencies of nucleic acid damage in a genome-wide context is integral to understanding the mechanisms of DNA repair, cellular aging, and cancer (Roos, et al. Trends Mol Med 12, 440-450 (2006); Schumacher, et al. Trends Genet 24, 77-85 (2008); O'Driscoll, Cold Spring Harb Perspect Biol 4 (2012)). Global nucleic acid damage assessment can be used to correlate damage with disease initiation and progression. Damage assessment is also useful for pharmaceutical and cosmetic industries in order to determine the damage potential of drugs and cosmetics.

Various methods have been developed to measure the bulk frequency of DNA damage in cellular populations (e.g. the Comet assay) (Kubo, et al. Biochemistry 31, 3703-3708 (1992); Collins, Mol Biotechnol 26, 249-261 (2004)). While bulk assays can identify DNA damage lesions and measure the relative overall level of damage, they fail to accurately quantify the frequency and location of DNA damage events. Short-read next generation sequencing (NGS) has been adapted to examine both the frequency and location of DNA damage on a genome-wide scale (reviewed in Sloan, et al., Trends Biotechnol (2018)). However, current short-read NGS methods to detect DNA damage have inherent experimental challenges that limit utility, such as the dependence on the availability and specificity of antibodies to capture DNA damage (Hu, et al. Genes Dev 29, 948-960 (2015)). Frequently, these sequencing methods only identify a single type of DNA damage, for example, only ribonucleotides (ribose-seq) (Koh, et al. Nat. Methods 12, 251-257 (2014)). In addition, these NGS workflows typically involve time-consuming library preparation, loss of strand information, low detection resolution, cumbersome data analysis, and frequently require high levels of DNA damage for detection (reviewed in Sloan, et al. (2018)). Most of these NGS methods require high levels of damage for reliable detection and thus are limited in their utility for analyzing low physiological levels of DNA damage. Long-read single molecule real-time (SMRT®) sequencing (PacBio, Menlo Park, Calif.), has been utilized to directly detect several DNA lesions on synthetic substrates (Clark, et al. Genome Integr. 2, 10 (2011)). Due to sequencing and analysis limitations, SMRT sequencing does not currently allow for the detection of stochastic DNA modifications on a genome-wide scale.

Methods to accurately and quantitatively detect DNA damage and evaluate repair efficiency are necessary to fully understand the cellular consequences of endogenous and exogenous DNA damaging agents and subsequent repair.

SUMMARY

In general, kits and compositions are provided that include a nucleotide (dNTP) mix that has one or a plurality of different modified nucleotides, a ligase, and a nick translating activity.

In general, methods are provided for detecting a nick by sequencing in a double-stranded nucleic acid preferably a double-stranded DNA. In some embodiments, the method comprises incubating a double-stranded nucleic acid (e.g. DNA) having a nick with one enzyme that provides a nick translating activity, or a plurality of enzymes that together provide a nick translating activity; a ligase; and a dNTP mix comprising a modified dNTP, to generate a nucleic acid product comprising a patch of newly synthesized nucleic acid containing a plurality of modified nucleotides that are at or adjacent to the site of the nick. In some embodiments, the method comprises the initial step of creating the nick in the double-stranded nucleic acid (e.g. DNA). The nick may be created at the site of a damaged or mismatched nucleotide within the double-stranded nucleic acid (e.g. DNA); such as by using one or more DNA repair enzymes as described herein. Different DNA repair enzymes have different specificities, and therefore the choice of DNA repair enzyme may depend on the damaged or mismatched nucleotide that is to be converted into a nick. The method may comprise detecting the nick by identifying the patch in the nucleic acid for example by sequencing. The choice of modified nucleotides for use in the nick translation step may depend on the detection method; for example, different sequencing techniques and platforms are capable of differentiating different modified nucleotides from the corresponding unmodified nucleotides.

The double-stranded nucleic acid may be double-stranded DNA, such as double-stranded genomic DNA and may be intact (e.g. a genome) or fragmented. The nucleic acid (e.g. DNA) fragments may be as large as 30 Kb or as small as 100 bases. The preferred size of the nucleic acid in which damaged nucleotides are to be identified and/or located depends on the sequencing platform selected. In one embodiment of the method, the nick in the nucleic acid results from treating a damaged nucleic acid with a single repair enzyme or a plurality of repair enzymes that recognize and hydrolyze phosphodiester bonds and cause a nick at or near to a damaged nucleotide.

In one embodiment, the one or more polymerases that provide a nick translating activity add(s) a number of nucleotides and modified nucleotides to the ends of the strands at the nick sites by nick translation. The ligase seals the newly added sequence of nucleotides with the 5' end of the downstream strand to form a nucleic acid product comprising a patch of nucleic acid comprising the modified nucleotides. The patch may be less than 5000 bases in length, for example, at least 5 bases up to 20, 50 or 100 bases in length, as desired, where the length of the patch can be modulated by varying the ratio of one or more polymerases that provide a nick translating activity and the ligase. The modified nucleotides incorporated in a patch may represent 25% of total bases in the patch if one type of modified nucleotide is used in a reaction mix, 50% if two types of modified nucleotide is used in a reaction mix, 75% is three types of modified nucleotide is used in a reaction mix and 100% if 4 types of modified dNTP is used in the reaction mix. The selection of modified nucleotides for use in generating the patch may be determined by the ability of the selected sequencing platform to differentiate the presence of modified bases from a corresponding non-modified bases. The detection by sequencing of the patch containing modified bases enables the sites of the nicks and the nucleic acid damage to be identified and mapped using computational approaches that include any of machine learning, artificial intelligence that utilize targeted algorithms.

In another embodiment, a method is provided that comprises an additional step of chemically or enzymatically treating the product described above to alter the identity and characteristics of the modified base or the unmodified base in the patch, but not both, prior to sequencing. The sequencing reads from treated and untreated control nucleic acid can then be compared to identify the location of the altered bases and hence locate the damaged bases in the nucleic acid.

A sequencing platform that can differentiate modified from unmodified bases can provide a sequence of the nucleic acid containing the patch which can be detected from its altered base content. The sequence of bases in the patch reveals the identity and location of the damaged base(s) in the nucleic acid including the particular strand on which the damage occurred.

Embodiments of the method provide means to detect nucleic acid damage on a genome-wide scale. Some embodiments include (1) detecting nicks or gaps produced by a variety of enzymes including repair enzymes, site specific nucleases, including nucleic acid guided nucleases such as Cas9, Argonaute or nuclease off-target nicking endonucleases, or non-specific nucleases; (2) mapping drug/chemotherapy (e.g. cisplatin) damage; (3) mapping mitochondrial DNA damage; (4) mapping mismatches; or (5) mapping DNA damage on open/closed chromosome. The method can also be used to analyze disease (e.g. cancer) progression because some diseases are associated with increased nucleic acid damage.

These and other features of the present teachings are set forth herein.

BRIEF DESCRIPTION OF THE FIGURES

The skilled artisan will understand that the drawings, described below, are for illustration purposes only. The drawings are not intended to limit the scope of the present teachings in any way. Although some of the drawings illustrate the use of the combination of methylated dATP/methylated dCTP (6mATP/4mCTP), this is not intended to be limiting. Any one or a plurality of modified nucleotides can be used in the methods and compositions of the invention. While the sequencing platform for NGS described in the figures are Pacific Biosystems and Illumina platforms, other sequencing platforms may be used.

After isolation of genomic DNA from an organism of interest (step 1), a NGS library is constructed for a desired sequencing platform here shown for a Pacific Biosystems sequencing platform (step 2). The library is then treated with one or more repair enzymes (e.g., one or more of the enzymes exemplified in Table 1) to create nicks (a gap of one or more nucleotides on one strand of a duplex nucleic acid) at damage sites (step 3). Repair enzymes may make a nick 5' or 3' to the damaged nucleic acid. Other repair enzymes may remove the damaged base and/or sugar creating an apurinic (AP) site that is removed by AP lyase activity to generate a nick. The sample is then nick translated in the presence of a DNA polymerase, DNA ligase and a dNTP pool including one or more modified nucleoside triphosphates. A patch of modified nucleotides is created in the nucleic acid library (step 4). In one embodiment, a patch of 30 nucleotides may include at least two, three or four modified nucleotides of the same or different type. The library is sequenced (step 5) and analyzed to locate and optionally map patches containing modified nucleotides, where the location of the patches reveals the nucleic acid damage sites (step 6).

Figure 1:
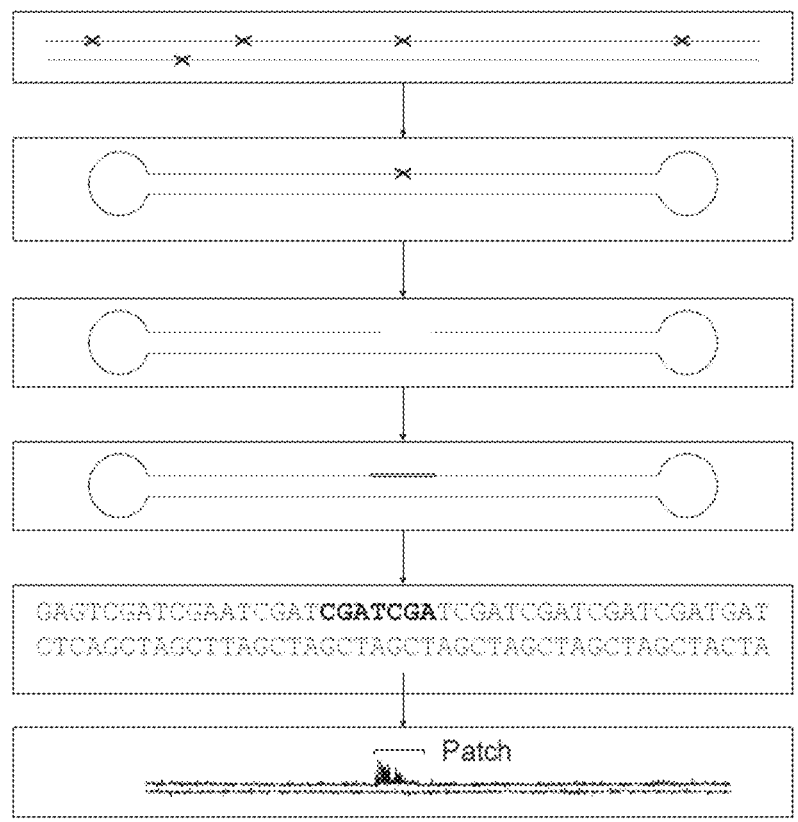
FIG. 1 is a biochemistry flow chart showing embodiments of the method in which a damaged site in a double-stranded DNA molecule (here exemplified by a genome) is converted into a patch of modified nucleotides that can be identified by DNA sequencing. The patch corresponds to the location, type and strand of damage. Top strand sequence: SEQ ID NO: 1; bottom strand sequence: SEQ ID NO: 2.
Figure 2:
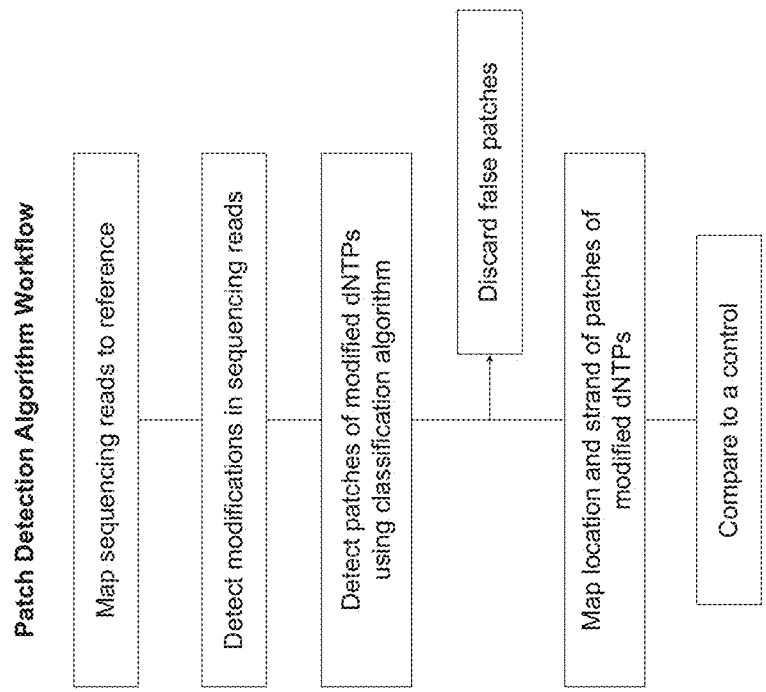

FIG. 2 is a data flow diagram of the computational steps that may be used to capture and label sequence data of nucleic acids in step 6 of FIG. 1. The sequence reads are mapped to a reference genome. (2) Modifications in the sequence reads are detected. (3) Patches of modified nucleotides are identified using a classification algorithm which can reject false patches. (3a) False patches are then discarded. (4) A sequence is generated which contains the location and strand of identified patches containing the modified nucleotides which (5) is compared to a control. A map is constructed in graphical form for the user.

FIG. 3A-3B provides an embodiment of the method in FIG. 1 and FIG. 2.

FIG. 3A shows the workflow to obtain a patched DNA at sites of DNA damage. Genomic DNA containing DNA damage (marked with an "x") is isolated from an organism of interest and PacBio libraries are created from isolated genomic DNA by shearing into 2 kb fragments and ligating SMRTbell® adapters (PacBio, Menlo Park, Calif.) to the genomic DNA fragments to form a library. The library DNA is treated with repair enzymes that result in nicks. Bst DNA polymerase, full length (Bst FL) (New England Biolabs, Ipswich, Mass.) then performs nick translation in the presence of a pool of nucleotides containing selected modified nucleotides (e.g. $d^{6m}ATP$ and $d^{4m}CTP$). Taq DNA ligase and NAD+ ligate the nick translated DNA to form a continuous strand that contains a patch of modified bases. Here the DNA is sequenced on a PacBio SMRT RSII or Sequel sequencer.

FIG. 3B shows a kinetic trace of high interpulse duration (IPD) ratios that reveals a 38 nucleotide patch of methylated bases on a genomic DNA top strand, in which the start of the patch (triangle) corresponds to a DNA damage site. The triangle indicates the nick site at the start of the patch on the top strand. Top strand sequence: SEQ ID NO: 3; bottom strand sequence: SEQ ID NO: 4.

FIG. 4A-4F shows genome-wide ribonucleotide detection.

FIG. 4A shows an experimental work flow for generating a patch of modified nucleotides at each ribonucleotide embedded in genomic DNA. Genomic DNA was obtained from *T. kodakarensis* and *E. coli* WT and ΔRNaseH2 genomic DNA in where ribonucleotides are expected to be present with increased frequency in the genome of the ΔRNaseH2 mutants than would otherwise occur stochastically in the wild type organism. Genomic DNA was fragmented and SMRTbell adaptors are ligated. The DNA was nicked with 9° N™, RNaseH2 (New England Biolabs, Ipswich, Mass.), and nick translated with Bst FL (also referred to herein as nucleotides) in the presence of a nucleotide mix containing modified nucleotides, Taq DNA ligase and NAD+ and sequenced on a PacBio sequencer.

FIG. 4B shows the detected ribonucleotides in wild type (white) and ΔRNaseH2 mutant genomes (shaded) following PacBio sequencing. The results are consistent with an expected low level of ribonucleotides in wild-type *T. kodakarensis* and *E. coli* genomes (~11 and ~2 rNs per Mb respectively), and a substantial increase in ribonucleotides in mutant genomes (~538 and ~21 rNs per Mb, respectively).

Figure 4C:
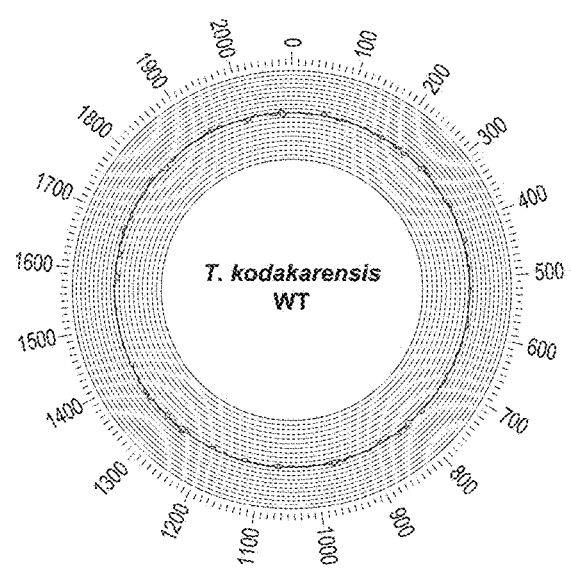

FIG. 4C shows the location of ribonucleotides visualized on a genome-wide scale for *T. kodakarensis* wild-type in circular plots.

Figure 4D:
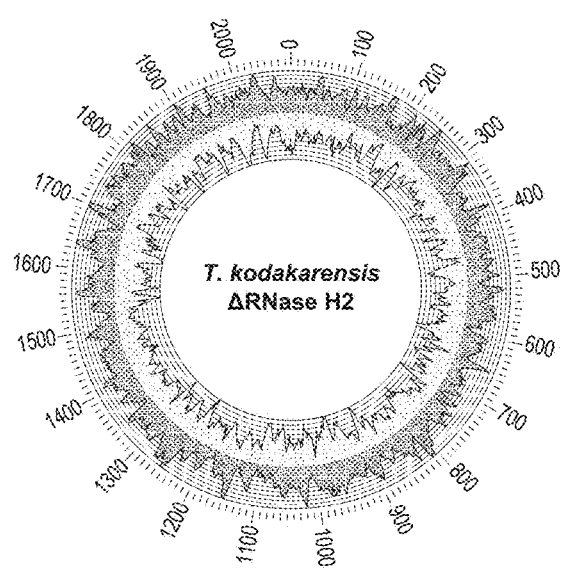

FIG. 4D shows the location of ribonucleotides visualized on a genome-wide scale for *T. Kodakarensis* ΔRNase H2 in circular plots.

Figure 4E:
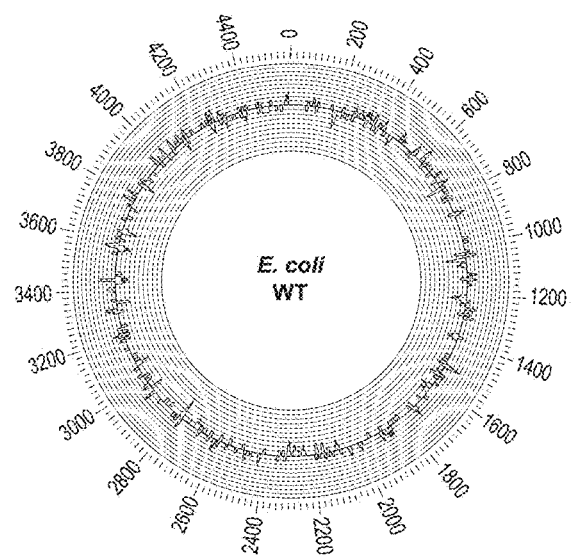

FIG. 4E shows the location of ribonucleotides visualized on a genome-wide scale for *E. coli* WT in circular plots.

Figure 4F:
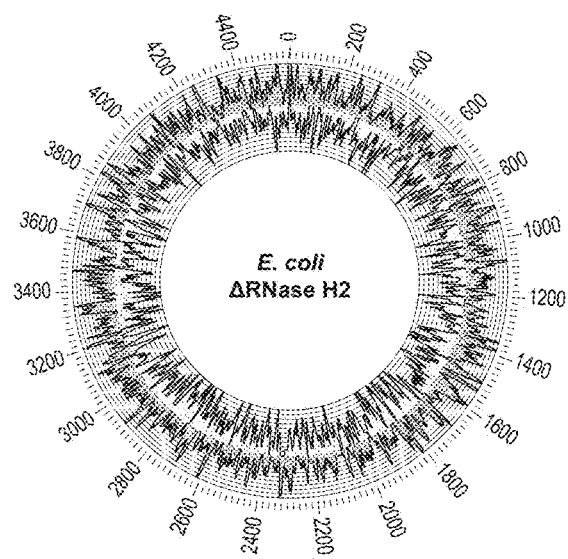

FIG. 4F shows the location of ribonucleotides visualized on a genome-wide scale for *E. coli* ΔRNase H2 in circular plots.

Circular plots were generated using Circos software (Krzywinski, M. et al. Genome Res 19:1639-1645 (2009)). The black and light grey line plots correspond to frequency of observed patches (per Mb) on the top and bottom strand, respectively. Frequency of patches was computed using rolling average with a 10 Kb window size.

Figure 5:
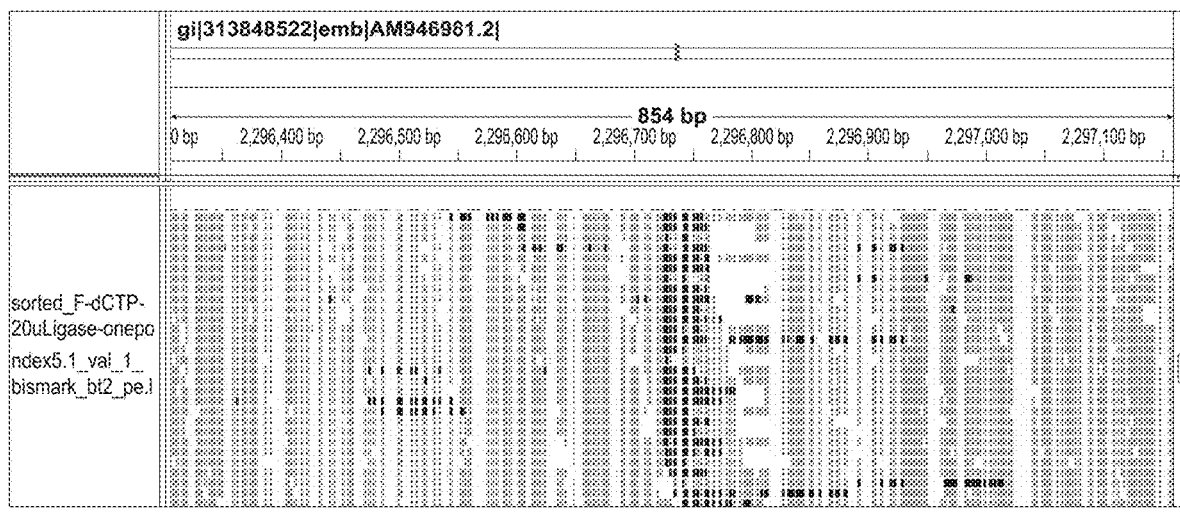

FIG. 5 is an Integrative Genomic Viewer (IGV) plot of an Nt.BstNBI nick site in the *E. coli* genome detected by Illumina sequencing. At nick sites, nick translation occurs in the presence of 5-formyl-dCTP to create a patch. Deamination converts all unmodified C's to uracil, while 5-formyl C's are not deaminated. The DNA is sequenced and mapped to an 854 bp region of the *E. coli* genome. Uracil residues are in gray and a patch of Cs are in black that correspond to the Nt.BstNBI nick site.

Figure 6B:
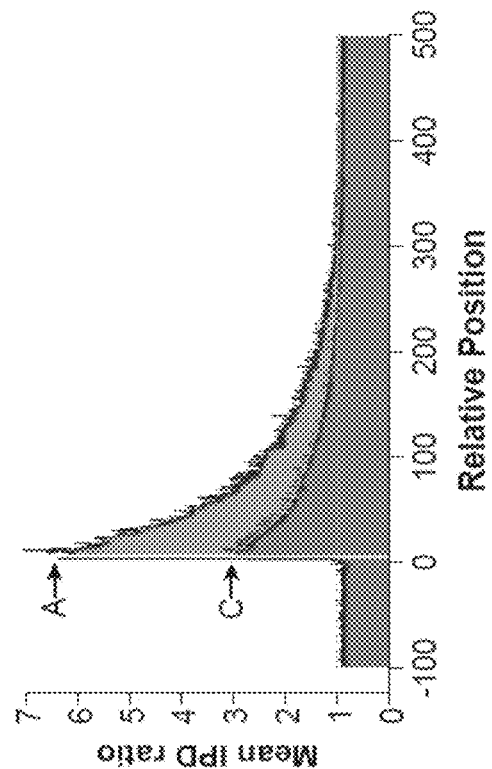
Figure 6C:
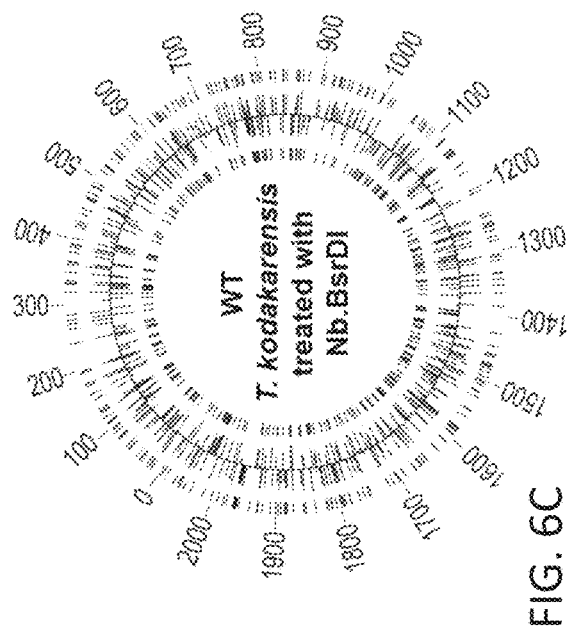
Figure 6A:
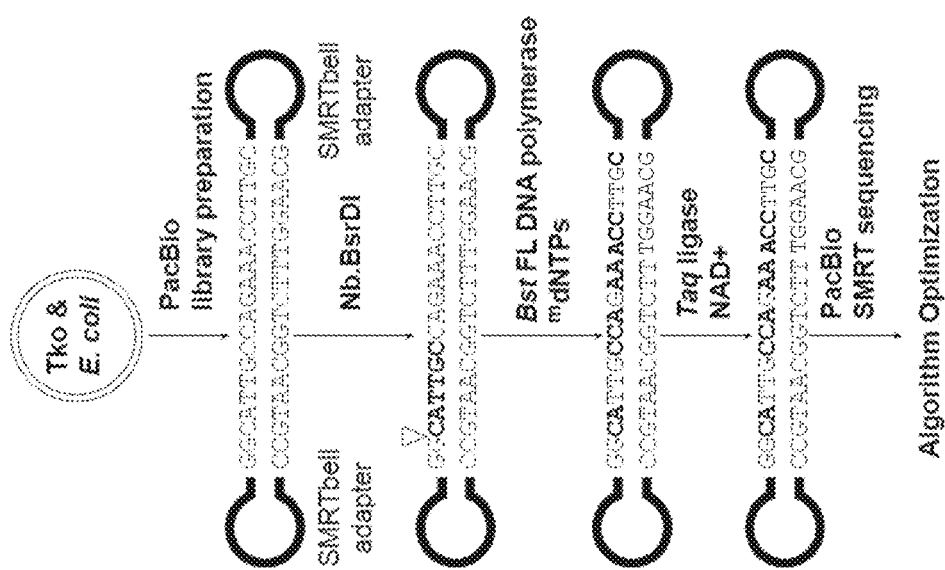

FIG. 6A-6C demonstrates detection of nick sites by patches in a control DNA that has been treated with a site-specific nicking endonuclease.

FIG. 6A shows the workflow to create 2 kb PacBio libraries from *T. kodakarensis* (Tko) and *E. coli* genomic DNA and SMRTbell adaptors. The genomic DNA was nick-translated with Bst FL and Taq DNA ligase in the presence of modified nucleotides after site specific nicking by Nb.BsrDI at 5'-NN|CATTGC-3'. The nick translated DNA was sequenced using a PacBio sequencer and the data analyzed as described in FIG. 2. Top strand sequence: SEQ ID NO: 5; bottom strand sequence: SEQ ID NO: 6.

FIG. 6B shows a plot of IPD signals in which the highest IPD ratios were observed immediately downstream to Nb.BsrDI nick sites and decreased further away from the nick site for single-molecule reads from *T. kodakarensis* genomic DNA. Average IPD ratios for A's and for C's are shown.

FIG. 6C shows a circular plot of known *T. kodakarensis* Nb.BsrDI sites across the entire genome correlated with the results obtained in FIG. 6A. Tick marks on the outermost and innermost rings correspond to the location of known nicking sites on the top and bottom strand, respectively. Histogram bins correspond to location of detected patches (and Nb.BsrDI sites accordingly). The binning intervals were set to 100 bases. The predicted and actual nick sites showed >95% correlation.

FIGS. 7A and 7B show two Circos plots comparing the location and frequency of patches which correspond to damaged nucleotides (here 8-oxo-Guanine) that were stochastic on a genome-wide scale, using *E. coli* MG1655 cells exposed to $H_2O$ or $H_2O_2$. The outer histogram shows frequency of patches at different genomic locations in the top strand, the inner histogram shows frequency of patches at different genomic locations in the bottom strand. Patches containing $^{4m}C$ and $^{6m}A$ were detected using Pacific Bioscience sequencing.

FIG. 7A shows the results after treatment with water.

FIG. 7B shows the results of oxidative damage caused by $H_2O_2$ that results in the formation of 8-Oxo-G.

FIG. 8A-8D show detection of stochastic genome-wide thymine dimers using methods described in FIG. 1 and FIG. 2. Black and grey line plots correspond to frequency of observed patches (per Mb) on the top and bottom strand, respectively. Frequency of patches was computed using rolling average with 10 Kb window size.

Figure 8A:
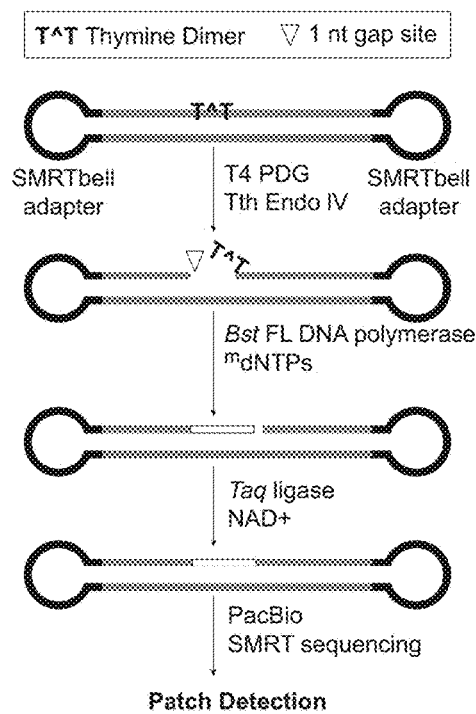

FIG. 8A provides the workflow for PacBio sequences of *E. coli* genomic DNA exposed to UV-radiation generating thymidine dimers.

Figure 8B:
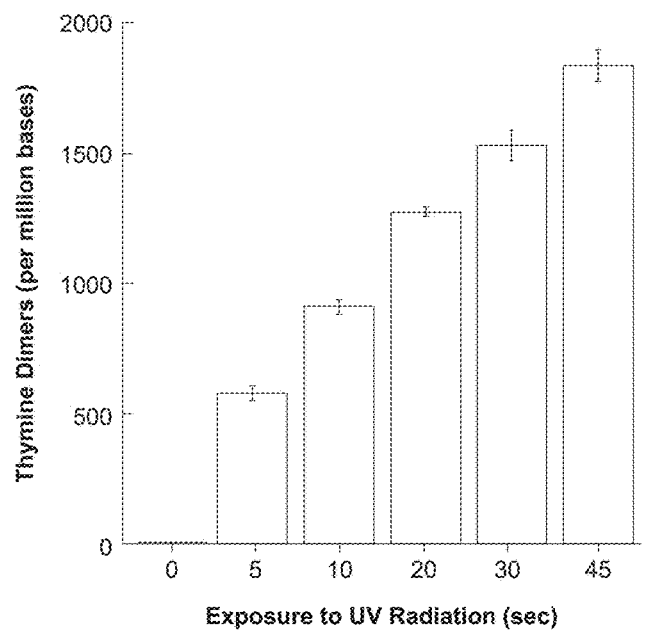

FIG. 8B shows the results of the workflow described in FIG. 8A where a linear increase in thymine dimers is observed when the exposure time to UV radiation was increased.

Figure 8C:
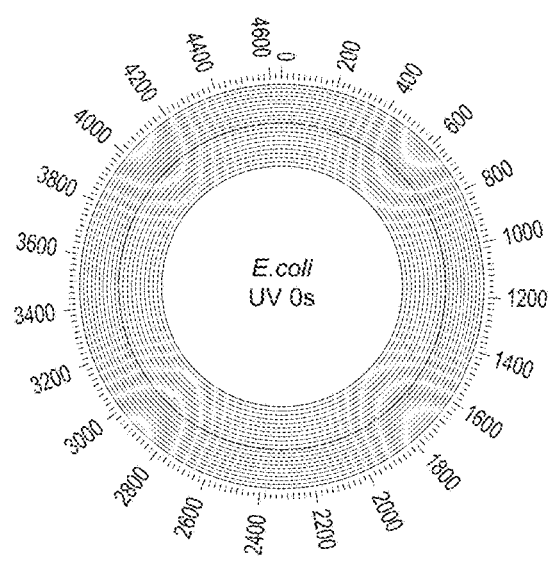

FIG. 8C shows the circular plot for the location of thymine dimers on a genome-wide scale where the genome was not previously exposed to UV irradiation.

Figure 8D:
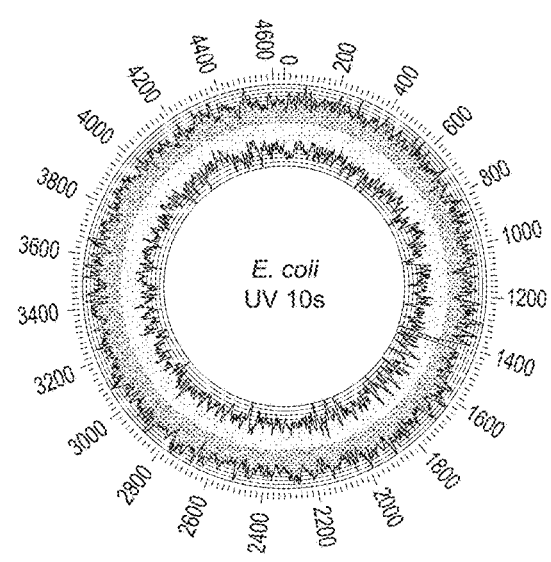

FIG. 8D shows the circular plot for the location of thymine dimers on a genome-wide scale where the genome was exposed to UV irradiation for 10 seconds.

FIG. 9A-9D shows how the methods described in FIG. 1 and FIG. 2 can be used for detection and mapping of *E. coli* replication initiation points.

FIG. 9A shows a schematic of *E. coli* PolI (black) and PolIII (grey) synthesis around the oriC, where PolI synthesizes primarily on the lagging strand, while PolIII synthesizes on both leading and lagging strands.

Figure 9B:
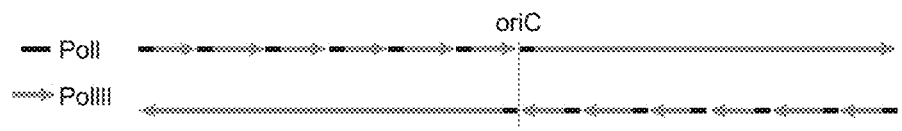
Figure 9B:
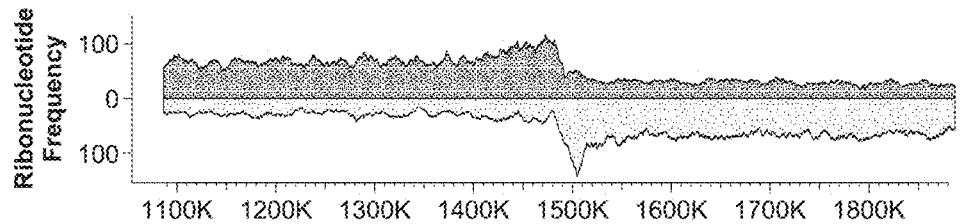

FIG. 9B shows how detection of ribonucleotide frequency obtained from analysis of *E. coli* PolI I709G/DRNaseH2, provided actual visualization of leading and lagging strand synthesis around OriC. The top strand is in black and bottom strands in grey, where a characteristic switch in number of ribonucleotides located on each strand is observed.

Figure 9C:
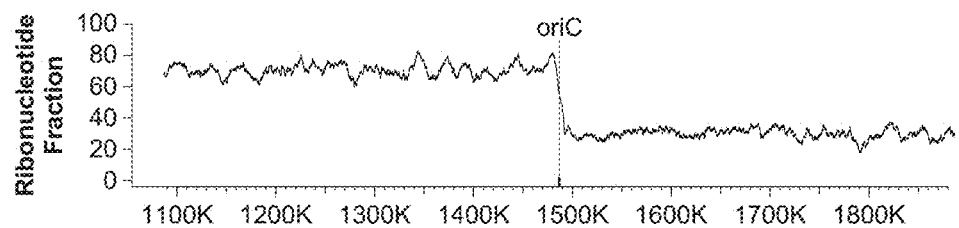

FIG. 9C shows how ribonucleotides found on the top strand varies along the genomic region surrounding the known oriC (vertical grey line), where a switch in ribonucleotide frequency at the oriC is observed.

Figure 9D:
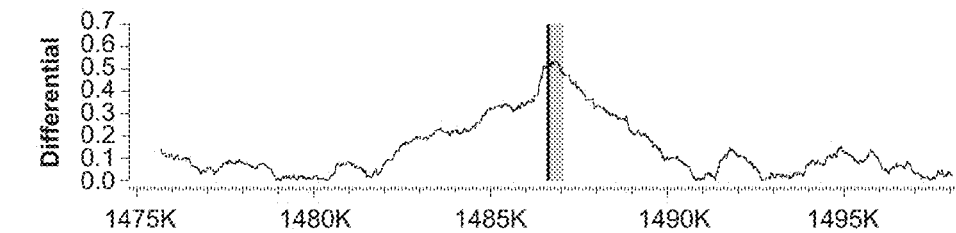

FIG. 9D shows the precise genomic location, in which ribonucleotide frequency switches were determined by locating the position with maximal value of differential. The vertical line corresponds to the lagging strand replication initiation point to the left of oriC while the grey area behind the vertical black line corresponds to the previously reported location of the oriC.

DETAILED DESCRIPTION

The ability to identify, quantify and locate DNA damage across a genome has become increasingly important to understand links between DNA damage, mutations and disease. In certain embodiments, any form of damage in the genome including common forms of damage and widespread damage in any single sample includes detection of rare damage events can be detected.

Embodiments provide a number of advantages. These include: a high-resolution view of global DNA damage across an entire genome; the ability to detect a wide variety of lesions, and the detection of damaged nucleotides in unamplified and unenriched DNA libraries that enables absolute quantitation of damage levels on a genome wide scale.

Embodiments of the compositions and methods include analysis of nucleic acids from various sources having a range of different types of damaged nucleotides. This depends on the availability of a suitable repair enzyme. A large number of repair enzymes are known with representative examples described herein. Once the repair enzyme has recognized a damaged nucleotide and excised it to form a nick, a suitable polymerase and ligase can repair the nick by nick translation incorporating a type of modified nucleotide that is suitable for detection in a sequencer. The selected modified nucleotide may be chosen from a range of modified nucleotides. Examples of polymerases, ligases and modified nucleotides are also provided herein. Examples 1-7 provide specific examples of DNA damage caused by oxidation events, nicking enzymes, ribonucleotide insertion, ultraviolet exposure and stochastic damage. The results show that embodiments are capable of detecting damaged sites throughout a genome with a high degree of efficiency using a variety of sequencing platforms.

Unless described otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

Although any methods and materials similar or equivalent to those described herein can be used in the practice or testing of the present invention, the preferred methods and materials are described.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Before various embodiments are described in greater detail, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the present disclosure.

Although any methods and materials similar or equivalent to those described herein can also be used in the practice or testing of the present teachings, exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

It must be noted that as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All publications, patents, and patent applications mentioned in this specification are herein incorporated by reference to the same extent as if each individual publication, patent, or patent application was specifically and individually indicated to be incorporated by reference.

As used herein, "a damaged nucleotide" refers to an aberrant nucleoside monophosphate in a nucleic acid that differs from a standard nucleoside monophosphates (C, A, G, or T) for example by an altered sugar or an altered or excised base or an altered base or bases through dimerization. Mismatches are also included. Examples are provided in Table 1. A mismatch refers to a lack of complementarity on opposing strands of 2 bases. The damage may be caused by environmental or chemical events. A "damaged site" refers to a position in the nucleic acid that is abnormal because a base or sugar has been modified, removed or mismatched.

Examples of modified sugars include those in which the deoxyribose is substituted with an alternate sugar or modified deoxyribose. Examples include ribose or alkylated ribose; replacement of one or more hydroxyl groups by halogen atoms, aliphatic groups, or functionalized group such as ethers, amines, or the like, in the sugar. Examples of commonly occurring damaged bases result from oxidative damage such as 8-oxo-guanine, cross links such as thymidine dimers, or mismatches (see for example, U.S. Pat. No. 8,158,388).

The nucleic acid may be any double-stranded nucleic acid, including genomic DNA, a fragment of a genomic DNA, or a double-stranded product obtained by amplification of genomic DNA, messenger RNA, or ribosomal RNA. Genomic DNA includes a DNA molecule fragment from a genome. It also refers to a DNA that contains a sequence that corresponds to a sequence in the genome.

A repair enzyme is an enzyme that nicks at the site of a damaged nucleotide, either on one side of the damaged nucleotide or on both sides of the damaged nucleotide. Examples of repair enzymes are provided in Table 1.

A DNA polymerase suitable for nick translation can include Family A and Family B DNA polymerases. They include DNA polymerases with 5'-3' exonuclease activity and polymerases with flap endonuclease activity. Examples are provided in Table 2. As used herein, the term "one or more enzymes having nick translating activity" or "polymerases capable of nick translating activity" here used interchangeably includes (i) a polymerase that does not displace the strand ahead of it but rather degrades the strand ahead of it using a 5'-3' exonuclease activity or (ii) the combination of a strand-displacing polymerase and a flap endonuclease, in which the polymerase synthesizes and displaces the strand ahead of it and the flap endonuclease then cleaves the displaced strand to leave a nick. DNA Polymerase I and Bst FL, are examples of polymerases capable of nick translating activity that have a 5'-3' exonuclease activity and nick translation activity. Table 2 lists examples.

A ligase suitable for nick translation is preferably, such as NAD+ dependent Taq DNA ligase, but may also be an ATP ligase such as T4 DNA ligase. As used herein, "ligase" refers to an enzyme that is capable of joining two separate single stranded nucleic acids in cis to reform an intact double stranded nucleic acid. Examples of ligases that may be used herein are provided in U.S. Pat. No. 8,158,388 and Table 3. In embodiments, the ligase is preferably compatible with the polymerase so that both enzymes are active at the same temperature, for example, DNA Polymerase I and T4 DNA ligase. If the initial nick translation reaction is done at a higher temperature (e.g., 40° C.-70° C.) than the ligation reaction, then Bst FL, and Taq ligase may be preferred.

In the context of the present method, the terms "ligate", "ligating", "seal" and "sealing" are intended to indicate that the 3' end of the growing strand (i.e., the strand being extended by the polymerase) is ligated to the 5' end of the downstream strand (i.e., the strand that is being cleaved by the 5' to 3' exonuclease activity of the polymerase, or an flap endonuclease activity).

The term "nucleotide" refers to nucleoside monophosphates or NMPs that are present in a nucleic acid molecule as well as nucleoside triphosphates or NTPs that are present in reaction mixes. As used herein, "a nucleotide mix" includes the four standard nucleotides—GTP, ATP, TTP and CTP which can be dNTPs or rNTPs or a subset of the four standard nucleotides and additionally a single or a plurality of modified nucleotides to enable a polymerase to extend a single strand by nick translation such that the newly synthesized nucleic acid contains a mixture of standard nucleotides and modified nucleotides which form a patch in the repaired duplex. In general, a modified nucleotide may have a modification on the base, or the 2'OH of the sugar or the alpha phosphate, where the modification can be distinguished from the 4 standard nucleotides in a sequencing reactions. In one example, the nucleotide mix contains any one or combination of a modified dGTP, a modified dATP, a modified dTTP, and a modified dCTP along with a complement of standard nucleotides. In one embodiment, a modified dATP or a modified dCTP, or a combination of a modified dATP and a modified dCTP may be used. In some embodiments, the one or more modified nucleotides may replace some or all the corresponding unmodified nucleotides. Preferably nucleotides and modified nucleotides have a 3' hydroxyl so that after they are added to the chain by the polymerase, the polymerase can continue to extend the chain and the ligase can achieve ligation of the chain to the downstream strand. In many embodiments, the method should not employ chain terminators. Once the nucleotide is incorporated into a nucleic acid, it may be referred to as a base.

Examples of modified nucleotides in the nucleotide mix are provided in Tables 4 and 5 and include methylated purines or pyrimidines, acetylated purines or pyrimidines, alkylated riboses or other heterocycles such as 5-methylcytosine (5mC), 5-hydroxymethylcytosine (5hmC), 5-formylcytosine (5fC), 5-carboxylcytosine (5caC), 5-bromocytosine, 5-propynylcytosine, 5-iodocytosine, 5-aminoallylcytosine, or 5-propargylaminocytosine, N6-methyladenine, N4-methylcytosine, 8-Oxo-2'-deoxyadenosine (8-oxo-dA), 8-Oxo-2'-deoxyguanosine (8-oxo-dG), O6-methylguanine (O6-m-dG), 1-methyladenine (1-m-dA), O4-methylthymine (O4-m-dT) and β-D-glucosyl-hydroxymethyluracil (Base J). Other bases may be readily used. In other embodiments an NTP mix may exclude modified nucleotides including an optically-detectable moiety or an affinity tag.

As used herein, the term "patch" refers to a newly synthesized nucleic acid that contains a string of newly added bases in one strand of a duplex nucleic acid. The patch is created by nick translation followed by ligation. The string of nucleotides that are incorporated during nick translation are complementary to the un-nicked strand. The ligase seals the 3' end of the string to an adjacent 5' end of the downstream strand. The nucleotides in a patch are covalently linked to each other as well as to nucleotides not part of the patch via phosphodiester bonds. In any embodiment, a patch may only occupy a relatively small fraction of the length of a long nucleic acid such as 10% or less, or 5%, although the size of the patch can be adjusted as desired. A molecule can contain more than one patch. The patch should be long enough to detect easily in sequence reads of long nucleic acids but not so long as to result in unnecessary information gathering. A patch may have at least two, three, four or more modified nucleotides per 30 nucleotide analysis window. A "long" patch might be at least one kilobase and may optionally be a fragment of a library derived from an entire genome.

As used herein, the term "nick" refers to a site of a broken phosphodiester bond in a single strand of a nucleic acid that is otherwise double-stranded. A nick contains a 3' hydroxyl and an adjacent 5' phosphate. In the context of this disclosure, the 3' hydroxyl and adjacent 5' phosphate can be immediately adjacent to one another, with no intervening bases on the other strand such that the ends can be ligated together. Alternatively, the hydroxyl and adjacent 5' phosphate can be spaced at a distance from one another by the equivalent of a deoxyribose phosphate group. The former type of nick is formed by cleavage of a phosphodiester bond in a double-stranded DNA molecule. The latter type of nick is formed by nucleotide excision.

As used herein, the term "nicking" involves breaking the phosphodiester bond on only one side of a nucleotide. In other cases, nicking involves breaking the phosphodiester bond on both sides of a nucleotide. In the later cases, nicking will result in a one nucleotide "gap" which is referred to as a nick in this disclosure.

As used herein, the term "nick site" refers to the site at which a double-stranded DNA molecule has been nicked.

As used herein, the term "nick translating" refers to a process in which a polymerase: extends one strand of a duplex nucleic acid (e.g. DNA) at the 3' hydroxyl at a nick site while, at the same time, the adjacent strand is degraded. In some embodiments, the polymerase itself may have a 5' to 3' exonuclease activity and, as such, the adjacent strand may be degraded by the polymerase. In other embodiments, the polymerase may be strand-displacing polymerase and the adjacent strand may be displaced and degraded by a flap endonuclease (e.g., Fen1). Both reactions result in a nick that "moves" along the double-stranded nucleic acid that can be sealed by a ligase.

As used herein, the term "at or adjacent to" means that the end of a "patch" of nucleic acid containing modified nucleotides is initiated at a site of a nick. Because nick translation is used, the patch should be 3' of the site of a nick. The nick is no longer present in the product of the present method, but the site of the nick (i.e., the location at which the nick was present, prior to nucleotide addition/sealing) is still present, and can be determined by identifying the location of the patch containing modified nucleotides.

The initiation of the patch is generally at the first modified nucleotide 3' to the nick site. This may be for example, 1, 2, 3, 4, 5, 6, 7, 8, 9 or 10 nucleotides from the nick as determined by sequencing.

As used herein, the term "plurality" refers to a group that contains at least 2 members. For example, a plurality of modified nucleotides means 2 or more modified nucleotides. In certain cases depending on the context, a plurality may have at least 2, at least 5, at least 10, at least 100, at least 1000, at least 10,000, at least 100,000, at least $10^6$, at least $10^7$, at least $10^8$ or at least $10^9$ or more members.

The term "sequencing" refers to a method by which the identity of at least 10 consecutive bases (e.g., the identity of at least 20, at least 50, at least 100 or at least 200 or more consecutive bases) of a polynucleotide are obtained.

In these embodiments, the location of the modified base in the sequence reads is by its kinetic signature. In these embodiments, the sequencing may be done using SMRT sequencing (which relies on a zero-mode waveguide (ZMW)), Oxford Nanopore which relies on altered conductance through a nanopore, Illumina or Ion Torrent sequencing that relies on sequencing by synthesis or other sequencing platform.

As used herein, the term "next generation sequencing" (NGS) refers to the so-called parallel sequencing-by-synthesis or sequencing-by-ligation platforms currently employed by Illumina, Life Technologies, Pacific Biosciences and Roche etc. NGS methods may also include nanopore sequencing methods or electronic-detection based methods such as Ion Torrent technology commercialized by Life Technologies.

As used herein, the term "in vitro" refers to a reaction that occurs in a vessel with isolated components, not in live cells.

In the context of a preparation, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; d) a combination that is in a form that is not found in nature, e.g., dried, freeze dried, crystalline, aqueous; and/or e) a combination that contains a component that is not found in nature. For example, a preparation may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

The term "reacting" refers to combining under conditions (e.g., a suitable temperature, time and conditions) that result in a reaction, e.g., nicking and/or nick translation, etc.

Other descriptions of terms may appear throughout the specification.

In some embodiments, the method comprises creating a nick at the site(s) of damage within the double-stranded nucleic acid (e.g. DNA). For example, the double-stranded nucleic acid (e.g. DNA), such as in the form of a nucleic acid sequence library (e.g. NGS library), may be treated with one or more repair enzymes (e.g., one or more of the enzymes exemplified in Table 1) to create nicks (a gap of one or more nucleotides on one strand of a duplex nucleic acid) at damage sites. Repair enzymes may make a nick 5' or 3' to the damaged nucleic acid. Other repair enzymes may remove the damaged base and/or sugar creating an apurinic (AP) site that is removed by AP lyase activity to generate a nick. The sample is then nick translated in the presence of a DNA polymerase (e.g. Bst polymerase), DNA ligase (e.g. Taq ligase), and a dNTP pool including one or more modified nucleotides (e.g. $d^{6m}ATP$ and $d^{4m}CTP$); thereby creating a double-stranded nucleic acid product comprising a patch containing modified nucleotides. By way of example, a patch of about 30 nucleotides may include at least two, three or four modified nucleotides of the same or different type. The patch comprising modified nucleotides is then detected; for example by sequencing the double-stranded nucleic acid product, and analyzing the sequence to locate and optionally map patches containing modified nucleotides, where the location of the patches reveals the location of the nucleic acid damage sites within the original double-stranded nucleic acid.

In some embodiments, the nucleic acid may be any double-stranded DNA, for example genomic DNA; or may be double-stranded RNA, for example from double-stranded RNA viruses for example the Reoviridae.

In some embodiments, the method comprises an initial step of isolating the nucleic acid (e.g. genomic DNA) from an organism of interest, and constructing a library of sequences (e.g. NGS library for a desired sequencing platform, such as a Pacific Biosystems sequencing platform). For example, a Pacific Biosystems library may be created by shearing the nucleic acid into fragments of about 2 KB, and ligating PacBio SMRTbell adapters to the nucleic acid fragments to form a library.

Nicked DNA (e.g. genomic DNA) can be made by treating an initial sample comprising double-stranded (genomic) DNA containing damaged nucleotides with one or more DNA repair enzymes (see for example, Table 1). Similarly, other double-stranded DNA or double-stranded RNA may be nicked at sites of nucleotide damage by repair enzymes. The type of repair enzyme capable of making a nick can also reveal the nature of the damage in the nucleic acid, because certain repair enzymes recognize certain lesions within the nucleic acid (e.g. as identified in Table 1).

Nicked genomic DNA made by treating an initial sample comprising double-stranded genomic DNA containing damaged nucleotides with one or more DNA repair enzymes (see for example, Table 1). Similarly, other double-stranded DNA or double-stranded RNA may be nicked at sites of nucleotide damage by repair enzymes. The type of repair enzyme capable of making a nick can also reveal the nature of the damage in the nucleic acid.

Other enzymes can also make nicks in nucleic acids at damaged nucleotides including mismatch sites or sites containing deletions or modifications that are the result of damage or sometimes epigenetic changes. These include sequence-specific or sequence-non-specific nicking endonuclease and nucleic acid-guided endonucleases (which often nick at sites that are off-target). In these embodiments, the term "nicking endonuclease" refers to a site specific enzyme that cleaves (e.g. nicks) either the top or bottom strands of a double-stranded nucleic acid at a random or nonrandom position in the nucleic acids. In some cases a nicking endonuclease will nick the bottom or top strand at a specific sequence on the nucleic acid. Some nicking endonucleases recognize methylated or hydroxymethylated nucleotides. Methods of making nicking endonucleases can be found in references for example, U.S. Pat. Nos. 7,081,358; 7,011,966; 7,943,303; 7,820,424. A description of nicking endonucleases can be found in a variety of publications (e.g., Bellamy, et al. J. Mol. Biol. 2005 345, 641-653; Heiter, et al., J. Mol. Biol. 2005 348, 631-640; Xu, et al., Proc. Natl. Acad. Sci. USA 2001 98, 12990-12995; Samuelson, et al., Nucl. Acids Res. 2004 32, 3661-3671; Zhu, et al., J. Mol. Biol. 2004 337, 573-583; Morgan, et al., Biol. Chem. 2000 381, 1123-1125; Chan, Nucl. Acids Res. 2004 32, 6187-6199; Sasnauskas, Proc. Natl. Acad. Sci. USA 2003 100, 6410-6415; Jo, et al., PNAS 2007 104:2673-2678; Xiao, et al., *Nucleic Acids Res.* 2007 35:e16; U.S. Pat. Nos. 7,081, 358; 6,191,267, US 2005/0136462, U.S. Pat. Nos. 7,943, 303, 8,163,529, WO 2006/047183 and WO 2008/0268507). In some embodiments, the nicking endonuclease used may be sensitive to a nucleotide modification (i.e., in which case it only cleaves at the unmodified nucleotide, e.g., cytosine, but not the modified nucleotide, e.g., methylcytosine).

A nicking enzyme can be made by inactivating one of the catalytic domains of an endonuclease. For example see U.S. Pat. No. 7,081,358. Another type of example is a programmable endonuclease, e.g., Cas9 or a functional equivalent thereof (such as Argonaute or Cpf1). For example, Cas9 contains two catalytic domains, RuvC and HNH. Inactivating one of those domains will generate a nicking enzyme. In Cas9, the RuvC domain can be inactivated by an amino acid substitution at position D10 (e.g., D10A) and the HNH domain can be inactivated by an amino acid substitution at position H840 (e.g., H840A), or at a position corresponding to those amino acids in other proteins. Such endonucleases may be Argonaute or Type I or Type II CRISPR/Cas endonucleases that are composed of two components: a nuclease (e.g., a Cas9 or Cpf1 endonuclease or variant or ortholog thereof) that cleaves the target DNA and a guide nucleic acid e.g., a guide DNA or RNA that targets the nuclease to a specific site in the target DNA (see, e.g., Hsu, et al., Nature Biotechnology, 31: 827-832 (2013)). Nicking enzymes of the type described above may recognize mismatches and also deletions or additions that are the result of damage to the nucleic acid.

Once a nick has been created at a target site on one strand of the duplex (at the site of a damaged or mismatched nucleotide), polymerase(s) (see for example, Table 2) and ligase(s) (see for example Table 3) in the reaction mixture nick translate the nucleic acid from the nick, incorporating modified nucleotides (see for example Table 4 and 5) contained in the reaction mix to create a patch in the duplex nucleic acid. The patch comprises a plurality of incorporated modified nucleotides, which can be detected. The patch containing modified nucleotides effectively amplifies the signal from the single damaged base when the sequence of the nucleic acid is obtained and analyzed.

The modified dNTP used in patch generation is chosen based on the ability of the sequencer to distinguish the modified nucleotide from the unmodified nucleotide. The sequencing platform chosen thus to some extent determines the choice of modified nucleotide for creating the patch.

For SMRT sequencing, the DNA molecules may be sequenced in real time with intrinsic sequencing rates of several bases per second and average read lengths in the kilobase range. In such sequencing methods, sequential base additions catalyzed by DNA polymerase into the growing complementary nucleic acid strand are detected with fluorescently labeled nucleotides. As described in detail in US 2016/0153038 and other publications, the kinetics of base additions and polymerase translocation are sensitive to the structure of the DNA double-helix, which is impacted by the presence of base modifications, (e.g., 5-MeC, S-hmC, base J, etc.) and other perturbations (secondary structure, bound agents, etc.) in the template. By monitoring the kinetics of base incorporation during the sequencing reaction, base modifications can be readily detected. Examples of bases that can be detected by SMRT sequencing include $d^{6m}ATP$ and $d^{4m}CTP$ and others listed in Table 4 below.

Modified bases can also be detected using nanopore-based sequencing. Nanopore-based sequencing methods are described in, e.g. Soni, et al. Clin Chem 53: 1996-2001 (2007), or as described by Oxford Nanopore Technologies. As a DNA molecule passes through a nanopore, each nucleotide on the DNA molecule obstructs the nanopore to a different degree, changing the magnitude of the current through the nanopore in different degrees (see for example, U.S. Pat. Nos. 5,795,782, 6,015,714, 6,627,067, 7,238,485 and 7,258,838 and U.S. patent application publications US 2006/003171 and US 2009/0029477). Like ZMW-based sequencing methods, modified bases can be readily detected by nanopore sequencing (see, e.g., Wescoe, et al., J Am Chem Soc 136, 16582-16587 (2014) and others).

In these embodiments, the nucleotides that have a modified base may comprise 5caC, 5mC, 4mC, 5hmC, 5fC or N6-methyladenine, for example, although many alternatives could be used instead (see for example Tables 4 and 5).

In some embodiments, the modified nucleotide within the double-stranded nucleic acid product may be identified by enzymatically-treating or chemically-treating the product to change the identity of either the modified nucleotide or a corresponding unmodified nucleotide, but not both; sequencing the enzymatically-treated or chemically-treated sample to produce a plurality of sequence reads; comparing the sequence reads to a reference sequence; and identifying the location of the nucleotides that have either changed or remained the same in the sequence reads, thereby identifying the location of the modified nucleotide. This method may be conveniently done using a dNTP mix for nick translation comprising a modified dNTP such as a 5'-modified cytosine (a cytosine modified at the 5' position), e.g., 5caC, 5mC, 5hmC, 5fC, 5-bromocytosine, 5-propynylcytosine, 5-iodocytosine, 5-aminoallylcytosine, 5-propargylaminocytosine, and $d^{4m}CTP$. Such nucleotides are resistant to deamination by sodium bisulfite and DNA deaminase. As such, these modified nucleotides can be incorporated into DNA, and the product can be treated with sodium bisulfite or a DNA deaminase (which changes the cytosines into uracil, and as such, cytosines are sequenced as thymine) and the modified nucleotide can be detected because it is sequenced as a cytosine. As would be apparent, these methods may be done using any suitable sequencing method, including Illumina's reversible sequencing method. Examples of modified nucleotides that are resistant to deamination are listed in Table 3 below.

In any embodiment of the method, the ratio of the amounts of polymerase and ligase used may be adjusted to produce patches of a particular size. In many embodiments, the patches made by the method may have a median size of 5 to 100, e.g., 6 to 50 nucleotides, although patches that are larger or smaller can be used in many embodiments. Each patch may contain, at least 2, at least 5 or at least 10 modified nucleotides. When the present method is used to analyze a genome, the median number of modified nucleotides in a patch may be in the range of 2-30, e.g. 3-20. The fragments that contain the patches may be from 100 bp to 30 kbp in length, e.g., 200 bp to 5 kb, although fragments may be of any length.

In some embodiments, nick translation may utilize one or more aqueous compositions of enzymes that may be formulated to provide optimal conditions for the activities of the enzymes. In certain embodiments, the enzyme composition may contain a buffering agent (e.g., Tris or the like), salt (e.g., $NaCl_2$ or the like), the salt of a divalent cation ($MgCl_2$ or the like) and other necessary components. In some embodiments, the enzymes may be immobilized for example by creating fusion proteins in which one part of the fusion protein binds to a matrix such as a bead or a column and the other part of the fusion protein is the active ligase, polymerase, and/or repair enzyme or nicking agent. An example of an affinity moiety of a fusion protein is a chitin binding domain, a SNAP-tag® (New England Biolabs, Ipswich, Mass.), a maltose binding domain or any other suitable binding domain known in the art (see for example Mohamad et al. Biotechnol Equip. March 4; 29(2): 205-220 (2015)).

In other embodiments the nucleic acid is immobilized prior to or after treatment with enzymes to facilitate the reactions and to assist in sequencing. Nucleic acid can be immobilized nonspecifically using clay particles (see for example, Paget, et al. EMS Microbiology Letters, Volume 97, Issue 1-2, 1, 31-39 (1992); Ensafi, et al. J. Mater. Chem. B, vol 2, p 3022 (2014)), or specifically by hybridization as well as other methods known in the art.

In some embodiments, the components of the composition(s) used in nick translation and ligation reactions may be dissolved in an aqueous solution that may comprise a buffering agent, such as a non-naturally occurring buffering agent, and other essential compounds required for activity of the enzymes in the composition. The composition may contain other components, e.g., glycerol. The concentration of the nucleotides in the composition may be in the range of 3 µM or 5 µM to 200 µM. In some embodiments, the relative activities of the polymerase and DNA ligase may be selected so that a certain number of bases (e.g., 5-100 bases) are added before the DNA ligase seals the 3' end of the growing strand to the 5' end of the adjacent strand.

Also provided by the present disclosure are kits for practicing the subject method as described above. In certain embodiments, a subject kit may contain a dNTP mix comprising one or more modified nucleotides (as described above), a DNA ligase (as described above) and a nick translating activity (one or more enzymes as described above). In some embodiments, the kit may further comprise a DNA repair enzyme that generates nicks in double-stranded nucleic acid (e.g. double-stranded DNA) at sites that correspond to damaged or mismatched nucleic acids.

The components of a kit may be combined in one container, or each component may be in its own container. For example, the components of the kit may be combined in a single reaction tube or in one or more different reaction tubes. The kit components may include one or more DNA repair enzyme used in embodiments of the methods and compositions, for example APE 1, hOGG1 Uracil deglycosylase, formamideopyrimidine DNA glycosylase (FPG), T4 pyrimidine dimer glycosylase, RNaseH2, alkyl adenine glycosylase, Endonuclease III, Endonuclease IV, Endonuclease V, Endonuclease VIII, T7 Endonuclease 1, SMUG, Thymine DNA glycosylase, EndoMS, NEIL1, NEIL2, XPF/ERCC1 and XPG, or other repair enzymes (see for example U.S. Pat. No. 8,158,388) The kit components may also include a ligase, modified nucleotides, and/or a polymerase as described herein. In some embodiments, the modified dNTP is not optically detectible (e.g., is not fluorescent) and/or does not contain an affinity tag (e.g., is not biotinylated). However, in certain embodiments, an optically detectable modified dNTP or one that contains an affinity tag may be used. The kit may also contain other reagents e.g., a reaction buffer. The enzymes may be in a storage buffer (e.g. combined in the same or different storage buffer), which may further contain a stabilizing agent, e.g. glycerol having a concentration of for example 10%, 20%, 30%, 40%, 50% or 60%.

In addition to above-mentioned components, the kit may further include instructions for using the components of the kit to practice the present method.

Embodiments of the method provide a way to analyze damaged nucleic acids e.g. on a genome-wide scale that has a number of applications. For example, embodiments of the method may be used to detect off-target nicks that are generated by a nucleic acid-guided endonuclease such as Cas9 or Argonaute. In these embodiments, a DNA sample containing intact (not nicked) double-stranded DNA may be incubated with the endonuclease and the location, strand, abundance and/or sequence specificity of the off-target activities of the endonuclease can be investigated using the method. In other embodiments, the method may be used to investigate (e.g., map) damage caused by compounds, e.g., compounds that are known to damage DNA such as chemotherapeutic agents such as platinum compounds (e.g. cisplatin). In these embodiments, isolated DNA (or cells containing the same) may be treated with the compound, and the DNA may be analyzed using the method to determine the location, strand, type and abundance of the damage. The method can also be used to investigate mitochondrial DNA damage, as well as DNA damage in chromatin (e.g., open or closed chromatin). The method can also be used to analyze disease (e.g. cancer) progression and may have a prognostic or therapeutic use. Use of the embodiments of the methods described herein may be used to detect DNA secondary structures such as hairpins and Holliday junctions, and for evaluation of more complex repair pathways such as nucleotide excision repair and transcription coupled repair.

Embodiments of the invention can be used to analyze cellular processes such as DNA replication. In one example, lagging strand DNA synthesis in *E. coli*, was tracked to determine the replication initiation start point and its location in reference to the oriC, 53 bp to the left (FIG. 9A-9D) (Kohara, et al. Nucleic Acids Res 13, 6847-6866 (1985)) showed that a replication bubble to the left of the oriC that enables initiation of lagging strand synthesis in the clockwise direction. Patch analysis revealed the point to the left of the oriC in which lagging strand synthesis starts and supports previous models of replication initiation (Kohara et al; 1985, Fang et al. Mol Cell 4, 541-553 (1999)). Replication initiation start points can also be studied in more complex organisms using methods described herein. Other applications will be apparent to one of ordinary skill in the art.

Figure 7:
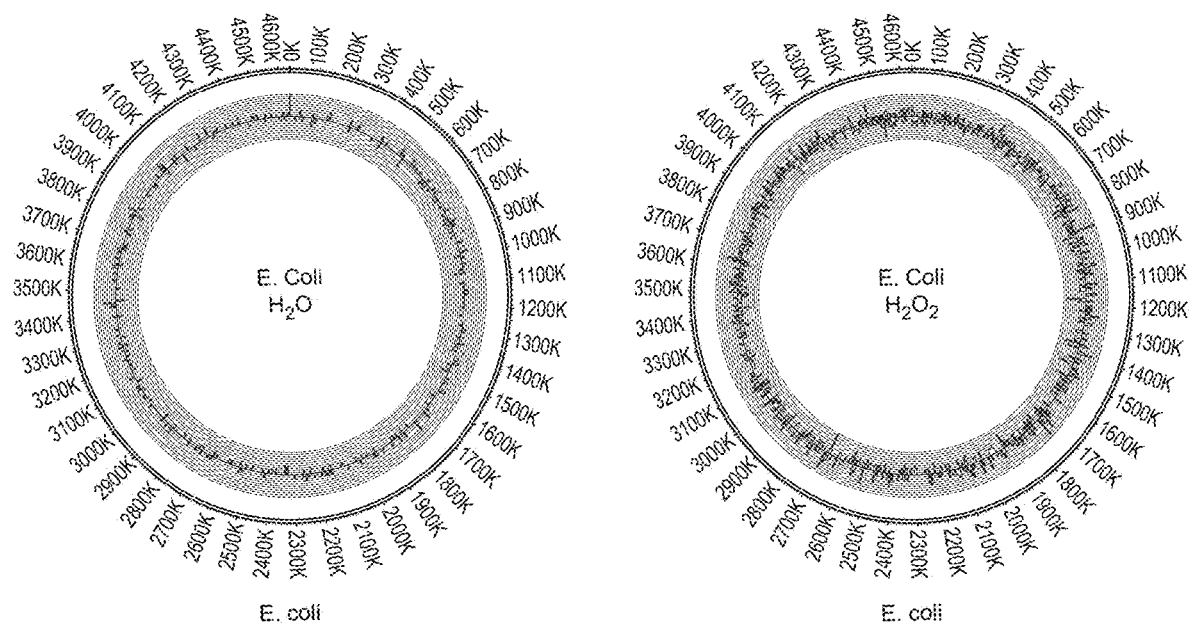

The accuracy, specificity and sensitivity of the patch analysis of damaged DNA has been verified in assays where the extent and type of damage is known in advance. Various sequencing platforms have been tested e.g. PacBio (see Examples 1-3, 5-7), Illumina platforms (Example 4) and Nanopore sequencing (Example 7). Mapping of different types of damage has been demonstrated. Examples 1 and 2 describe detection of ribonucleotides substituted for deoxynucleotides in mutant cells (ΔRNaseH2) that make the substitution of ribonucleotides for deoxynucleotides on each strand (see FIG. 4A-4F) for a bacterial genome (*E. coli* mutant) and a archaeal genome (*T. kodakarensis* mutant). In Example 2, the test further includes a Pol1 mutant. This provides an accurate detection of the origin of replication (oriC) as demonstrated in FIG. 9A-9D. Example 3 and FIG. 7 show detection of 8-oxo-dG (an oxidized form of dG). Examples 4-5 describe detection of nicking enzyme induced nicks using Illumina and Pac Bio platforms for sequencing and patch detection (FIG. 5, 6A-6C). Example 6 describes an assay for thymine dimers that result from UV irradiation (FIG. 8A-8D). Example 7 shows how to detect stochastic damage using nanopore sequencing.

The nucleic acid analyzed by the method may be from any source. In certain cases, the nucleic acid may be obtained from a culture of cells, e.g., a cell line. In other cases, the cells may be isolated from an individual (e.g., a patient). The cells may be isolated from a soft tissue or from a bodily fluid, or from a cell culture that is grown in vitro. In particular embodiments, the nuclei may be isolated from a soft tissue such as brain, adrenal gland, skin, lung, spleen, kidney, liver, spleen, lymph node, bone marrow, bladder, stomach, small intestine, large intestine or muscle, etc. Bodily fluids include blood, plasma, saliva, mucous, phlegm, cerebral spinal fluid, pleural fluid, tears, lacteal duct fluid, lymph, sputum, cerebrospinal fluid, synovial fluid, urine, amniotic fluid, and semen, etc. In some embodiments, the chromatin may be from a tissue biopsy obtained from a patient. Biopsies of interest include both tumor and non-neoplastic biopsies of skin (melanomas, carcinomas, etc.), soft tissue, bone, breast, colon, liver, kidney, adrenal, gastrointestinal, pancreatic, gall bladder, salivary gland, cervical, ovary, uterus, testis, prostate, lung, thymus, thyroid, parathyroid, pituitary (adenomas, etc.), brain, spinal cord, ocular, nerve, and skeletal muscle, etc. As would be apparent, the nucleic may be double-stranded nucleic acid (e.g. DNA) that has not been amplified. In other embodiments, the nucleic acid used in the method may be a PCR product. In some embodiments, the method may be used to analyze chromatin.

The present method may be used to analyze nucleic acid (e.g. DNA) from archaea, prokaryotes and eukaryotes, including yeast, plants and animals, such as fish, birds, reptiles, amphibians and mammals. In certain embodiments, the nucleic acid e.g. DNA, may be from mammalian cells, i.e., cells from mice, rabbits, primates, or humans, or cultured derivatives thereof.

The relationship between DNA damage and mutational rates in the target genome can be correlated in normal and variant cell types by determining both the sequence and damage status at each base across the genome.

Spontaneous nicks have been found to occur at no more than 1, 2, or 3 patches per $10^6$ bases (see Example 7). Once a patch has been identified, the damaged nucleotide at the nick site can be identified at a position that is less than 15 bp from the nick in at least 85%, for example, at least 90% or at least 95% of the patches. Preferably 95% of the patches are located less than 15 bp from the nick site. In particular, at least 70%, 75%, 80% or 85% of the patches are initiated less than 3 bp for example 2 bp from the nick site. Moreover in one embodiment, at least 90% with a SD of 3 of patches are on target with respect to the nick site.

As discussed above, the present method converts DNA lesions (e.g. damaged and/or mismatched nucleotides) to patches of modified nucleotides (e.g. having modified bases), which multiplies the signal and allows for confidence in distinguishing a patch created by the present method from random modification detection noise.

The examples provided below provide an illustration of the specificity and selectivity of patches for detecting damaged nucleotides. This has been shown by analyzing control DNA that has been treated with (a) UV irradiation (b) ribonucleotide substitution in RNAse mutants, (c) site specific nicking endonucleases, (d) 8-oxo-dG lesions.

TABLE 1

Enzymes (or enzyme mixtures) that create site specific nicks or gaps at DNA lesions

| Enzyme | Substrate | Cleavage location |
|---|---|---|
| APE 1 | AP sites | 1st phosphodiester bond 5' to the lesion |
| Endo III | Oxidized Pyrimidines, AP sites | 1st phosphodiester bond 3' to the lesion |
| Endo IV | AP sites | 1st phosphodiester bond 5' to the lesion |
| Endo V | Deoxyinosine, mismatches, hairpin/unpaired loop, flaps, pseudo Y structures | 2nd or 3rd phosphodiester bond 3' to the lesion |
| Endo VIII | Oxidized Pyrimidines, AP sites | 1st phosphodiester bond both 5' and 3' to the lesion |
| Fpg | Oxidized Purines, AP sites | 1st phosphodiester bond both 5' and 3' to the lesion |
| hOGG1 | Oxidized Purines, AP sites | 1st phosphodiester bond 3' to the lesion |
| hNEIL1 | Oxidized Pyrimidines and Purines, AP sites | 1st phosphodiester bond both 5' and 3' to the lesion |
| T7 Endo I | Cruciform, Holliday junctions, mismatches, heteroduplexes | 1st, 2nd or 3rd phosphodiester bond 5' to the mismatches |
| T4 PDG | Pyrimidine Dimers | N-glycosidic bond of the 5' Thymine of the dimer and the 1st phosphodiester bond 3' to the AP site |
| UDG | Deoxyuridine | N-glycosidic bond |
| hSMUG1 | Deoxyuridine, 5-hyroxyuracil, 5-hydroxymethyluracil, 5-formyluracil | N-glycosidic bond |
| hAAG | Deoxyinosine, Alkylated purines | N-glycosidic bond |

TABLE 2

Nick Translation polymerases

| I. DNA polymerases with 5'-3' exonuclease activity | II. DNA polymerases with strand displacement activity (requires flap endonuclease, e.g., Fen 1) |
|---|---|
| Family A DNA polymerases (requires flap endonuclease, e.g., Fen 1) | |
| *E. coli* DNA polymerase I | Bst DNA polymerase, Large Fragment |
| Taq DNA polymerase | Bsu DNA polymerase, Large Fragment |
| Bsu DNA polymerase, Full Length | Klenow Fragment DNA polymerase |
| Bst DNA polymerase, Full Length | KlenTaq DNA polymerase |

TABLE 2-continued

Nick Translation polymerases

| I. DNA polymerases with 5'-3' exonuclease activity | II. DNA polymerases with strand displacement activity (requires flap endonuclease, e.g., Fen 1) |
|---|---|
| | Bst 2.0 DNA polymerase |
| | Bst 3.0 DNA polymerase |
| | Bsm DNA polymerase, Large Fragment |
| | Klenow Fragment DNA polymerase, exo- |
| | Hemo KlenTaq |
| | Family B DNA polymerases (requires flap endonuclease, e.g., Fen 1) |
| | phi29 DNA polymerase |
| | Q5 ® DNA polymerase |
| | Vent ® DNA polymerase |
| | Deep Vent DNA polymerase |
| | Phusion ® DNA polymerase |
| | Vent DNA polymerase exo- |
| | Deep Vent DNA polymerase exo- |
| | Pfu DNA polymerase |

TABLE 3

Nick Sealing DNA ligases
Nick Sealing DNA ligases

Taq DNA ligase
E. coli DNA ligase
T3 DNA ligase
T7 DNA ligase
9°N DNA ligase
T4 DNA ligase
Human Ligase 1
Human Ligase 3

TABLE 4

Modified nucleotides detected by DNA sequencing platforms

| Modified nucleotide | Sequencing method | References |
|---|---|---|
| 5-carboxylcytosine (5caC) | Oxford Nanopore | (20) |
| 5-methylcytosine (5mC) | Oxford Nanopore, Pacific Biosciences | (17, 20) |
| 5-hydroxymethylcytosine (5hmC) | Oxford Nanopore, Pacific Biosciences | (17, 20, 21) |
| 5-formylcytosine (5fC) | Oxford Nanopore | (20) |
| N6-methyladenine | Oxford Nanopore, Pacific Biosciences | (17, 22) |
| N4-methylcytosine | Pacific Biosciences | (16) |
| 8-Oxo-2'-deoxyadenosine (8-oxo-dA) | Pacific Biosciences | (10) |
| 8-Oxo-2'-deoxyguanosine (8-oxo-dG) | Pacific Biosciences | (10) |
| O6-methylguanine (O6-m-dG) | Pacific Biosciences | (10) |
| 1-methyladenine (1-m-dA) | Pacific Biosciences | (10) |
| O4-methylthymine (O4-m-dT) | Pacific Biosciences | (10) |
| β-D-glucosyl-hydroxymethyluracil (Base J) | Pacific Biosciences | (23) |

TABLE 5

Modified nucleotides resistant to deamination
Modified nucleotide

| | |
|---|---|
| 5-carboxylcytosine | |
| 5-methylcytosine | |
| 5-hydroxymethylcytosine | $N^6$-Methyladenine |
| 5-formylcytosine | 4-Methylcytosine |
| 5-bromocytosine | 8-Oxoguanine |
| 5-propynylcytosine | 8-Oxoadenine |
| 5-iodocytosine | $O^6$-Methylguanine |
| 5-aminoallylcytosine | 1-Methyladenine |
| 5-propargylaminocytosine | $O^4$-Methylthymine |
| | 5-Hydroxyuridine |
| | 5-Carboxycytosine |
| | $N^2$-Methylguanine |
| | 6-Thioguanine |
| | 4-Thiothymine |
| | 2-Thiothymine |
| | 5-Aminoallyluridine |
| | 5-Propynyluridine |

All publications, patents, and patent applications mentioned in this specification including U.S. Provisional Application No. 62/586,932, filed Nov. 16, 2017, are herein incorporated by reference to the same extent as if each individual publication, patent, or patent application was specifically and individually indicated to be incorporated by reference.

EMBODIMENTS

Embodiment 1. A method comprising: (a) incubating a double-stranded nucleic acid having a nick with: (i) one or more enzymes that provide a nick translating activity, (ii) a ligase; and (iii) a dNTP mix comprising a modified dNTP to generate a nucleic acid product comprising a patch of newly synthesized nucleic acid containing a plurality of modified nucleotides that are at or adjacent to the site of the nick.

Embodiment 2. The method of embodiment 1, wherein the method comprises, prior to step (a): treating a double-stranded nucleic acid that has at least one damaged nucleotide with one or more DNA repair enzymes to convert the damage nucleotide to a nick.

Embodiment 3. The method of any prior embodiment, further comprising sequencing the product.

Embodiment 4. The method of any prior embodiment, identifying the location of the nick by analyzing the location of the patch.

Embodiment 5. The method of any of embodiments 2-4, further comprising determining the identity of the damaged nucleotide based on the selection of DNA repair enzyme.

Embodiment 6. The method of any prior embodiment, further comprising selecting a modified nucleotide capable of being differentiated from the unmodified nucleotide by a sequencing platform.

Embodiment 7. The method of any prior embodiment, further comprising: enzymatically-treating or chemically-treating the product to change the identity of either the modified base or a corresponding unmodified base, but not both; sequencing the enzymatically-treated or chemically-treated sample to produce a plurality of sequence reads; comparing the sequence reads to a reference sequence; and identifying the location of bases that have either changed or remained the same in the sequence reads, thereby identifying the location of the modified base.

Embodiment 8. The method of embodiment 7, wherein the modified dNTP comprises a 5-modified cytosine.

Embodiment 9. The method of embodiment 8, wherein the modified dNTP comprises 5caC, 5mC, 5hmC, 5fC, 5-bromocytosine, 5-propynylcytosine, 5-iodocytosine, 5-aminoallylcytosine, or 5-propargylaminocytosine.

Embodiment 10. The method of any of embodiments 7-9, wherein the enzyme or chemical treatment is a sodium bisulfite treatment.

Embodiment 11. The method of any of embodiments 7-9, wherein the enzyme or chemical treatment is a treatment with a DNA deaminase.

Embodiment 12. The method of any of embodiments 2-11, wherein the DNA repair enzymes include one or more of APE 1, Endo III, Endo IV, Endo V, Endo VIII, Fpg, hOGG1, hNEIL1, T7 Endo I, T4 PDG, UDG, hSMUG1 or hAAG.

Embodiment 13. The method of any prior embodiment, wherein the modified nucleotide is not fluorescent or biotinylated.

Embodiment 14. The method of any prior embodiment, wherein the nick translation is done using Bst FL or DNA polymerase I.

Embodiment 15. The method of any of embodiments 11-13, wherein the nick translation is done using a strand-displacing polymerase and a flap endonuclease.

Embodiment 16. The method of any prior embodiment, wherein the modified dNTP does not comprise an optically-detectable moiety or an affinity tag.

Embodiment 17. A kit comprising: a dNTP mix comprising one or more modified nucleotides; a DNA ligase; and a nick translating activity.

Embodiment 18. The kit of embodiment 17, wherein the modified dNTP comprises a 5-modified cytosine.

Embodiment 19. The kit of any of embodiments 17-18, wherein the modified dNTP comprises 5caC, 5mC, 5hmC, 5fC, 5-bromocytosine, 5-propynylcytosine, 5-iodocytosine, 5-aminoallylcytosine, or 5-propargylaminocytosine.

Embodiment 20. The kit of any of embodiments 17-19, wherein the kit further comprises a DNA repair enzyme.

Embodiment 21. The kit of any of embodiments 17-20, wherein the modified nucleotide is not fluorescent or biotinylated.

Embodiment 22. The kit of any of embodiments 17-21, wherein the nick translating activity is provided by Bst FL or DNA polymerase I.

Embodiment 23. The kit of any of embodiments 17-21, wherein the nick translating activity is provided by a strand-displacing polymerase and a flap endonuclease.

Embodiment 24. The kit of any of embodiments 17-23, wherein the modified dNTP does not comprise an optically-detectable moiety or an affinity tag.

Embodiment 25. The kit of any of embodiments 17-24, further comprising a DNA repair enzyme that generates nicks in double-stranded DNA at sites that correspond to damaged nucleotides.

Embodiment 26. The kit of embodiment 25, wherein the kit comprises include one or more of APE1, Endo III, Endo IV, Endo V, Endo VIII, Fpg, hOGG1, hNEIL1, T7 Endo I, T4 PDG, UDG, hSMUG1 or hAAG.

Embodiment 27. A composition comprising: a dNTP mix comprising one or more modified nucleotides, a DNA ligase and a nick translating activity.

Embodiment 28. The composition of embodiment 27, wherein the modified dNTP comprises a 5-modified cytosine and/or a 6-methyl adenine and 4-methyl cytosine.

Embodiment 29. The composition of any of embodiments 27-28, wherein the modified dNTP comprises 5caC, 5mC, 5hmC, 5fC, 5-bromocytosine, 5-propynylcytosine, 5-iodocytosine, 5-aminoallylcytosine, or 5-propargylaminocytosine.

Embodiment 30. The composition of any of embodiments 27-29, wherein the modified nucleotide is not fluorescent or biotinylated.

Embodiment 31. The composition of any of embodiments 27-30, wherein the nick translation is done using Bst FL or DNA polymerase I.

Embodiment 32. The composition of any of embodiments 27-30, wherein the nick translation is done using a strand-displacing polymerase and a flap endonuclease.

Embodiment 33. The composition of any of embodiments 27-32, wherein the modified dNTP does not comprise an optically-detectable moiety or an affinity tag.

Embodiment 34. The composition of any of embodiments 27-32, further comprising a nicked double-stranded nucleic acid.

Embodiment 35. A composition comprising a plurality of nucleic acid molecules, wherein at least some of the molecules comprise one or more patches that comprise newly synthesized nucleic acid containing a plurality (e.g., at least 2, at least 5 or at least 10 modified nucleotides) of modified nucleotides.

Embodiment 36. A method comprising: nick translating a double-stranded nucleic acid comprising a nick in a reaction mix that comprises: one or a plurality of enzymes that provide nick translating activity, a nucleotide mix comprising at least one modified nucleotide and a ligase, wherein nick translation is initiated at the nick, a plurality of the at least one modified nucleotide is incorporated at or adjacent to the nick during nick translation and the ligase seals the nick translated nucleic acid.

Embodiment 37 wherein Embodiment 36 further comprises creating the nick by treating a double-stranded nucleic acid that has at least one damaged or mismatched nucleotide with one or more nucleic acid repair enzymes to convert the damage or mismatched nucleotide to a nick. In further embodiments, the damaged or mismatched nucleotide may arise from a stochastic event or be the result of targeted damage such as might occur as a result of an agent that targets specific nucleic acid sequences. (A "stochastic" event may refer to an event that is randomly determined, having a random probability distribution or pattern that may be analyzed statistically but may not be predicted precisely).

Embodiment 37 wherein preceding embodiments further comprise sequencing the nick translated nucleic acid.

Embodiment 38 wherein preceding embodiments further comprise identifying a patch of sequence that comprises a plurality of the at least one modified nucleotides.

Embodiment 39 wherein preceding embodiments further comprise identifying the location of the nick by analyzing the location of the patch from the sequence that comprises the plurality of the at least one modified nucleotide.

Embodiment 39 wherein preceding embodiments further comprise determining the identity of the damaged or mismatched nucleotide based on the selection of nucleic acid repair enzyme.

Embodiment 40 wherein preceding embodiments further comprise selecting one or more modified nucleotides capable of being differentiated from the corresponding unmodified nucleotide by a sequencing platform Embodiment 41 wherein preceding embodiments further comprise:
(a) enzymatically-treating or chemically-treating the nick translated nucleic acid to change the identity of either the modified base or a corresponding unmodified base, but not both;

(b) sequencing the enzymatically-treated or chemically-treated nucleic acid from (a) to produce a plurality of sequence reads;
(c) comparing the sequence reads to a reference sequence; and
(d) identifying the location of bases that have either changed or remained the same in the sequence reads, thereby identifying the location of the modified base.

Embodiment 42 wherein preceding embodiments further comprise treating the modified nucleic acid with one or more enzymes selected from an oxidase, a deaminase and a beta glucosyltransferase or with chemical treatment using sodium bisulfite.

Embodiment 43 wherein preceding embodiments further comprise selecting one or more nucleic acid repair enzymes from the group consisting of: APE 1, Endo III, Endo IV, Endo V, Endo VIII, Fpg, hOGG1, hNEIL1, T7 Endo I, T4 PDG, UDG, hSMUG1 and hAAG.

Embodiment 44 wherein preceding embodiments further comprise nick translating the nucleic acid using Bst FL or DNA polymerase I.

Embodiment 45 wherein preceding embodiments further comprise the one or a plurality of enzymes providing nick translating activity include a strand-displacing polymerase and a flap endonuclease.

Embodiment 46 wherein preceding embodiments further comprise detecting to a first degree of confidence the position and identity of a damaged nucleotide in the double-stranded nucleic acid.

Embodiment 47 wherein the double-stranded nucleic acid in preceding embodiments further comprise a genomic DNA or derived from genomic DNA.

Embodiment 48 wherein the modified nucleotide in preceding embodiments comprises a 5-modified cytosine.

Embodiment 49 wherein the modified nucleotide in preceding embodiments are selected from the group consisting of 5-carboxylcytosine, 5-methylcytosine, 5-hydroxymethylcytosine, 5-formylcytosine, 5-bromocytosine, 5-propynylcytosine, 5-iodocytosine, 5-aminoallylcytosine, or 5-propargylaminocytosine.

Embodiment 50A is a kit that comprises:
(a) a nucleotide mix comprising one or more modified nucleotides;
(b) a ligase; and
(c) one or a plurality of enzymes that provide nick translating activity, wherein the nucleotide mix, ligase and one or a plurality of enzymes are contained in a single container or reaction vessel or in one or more different containers or reaction vessels.

Embodiment 50B. The kit of previous embodiments, further comprising one or more repair enzymes that generate nicks in double-stranded nucleic acid at sites that correspond to damaged or mismatched nucleotides.

Embodiment 50C. The kit of any of embodiments 50 A-B, wherein the modified nucleotide(s) compromise 6-methyl adenine and 4-methyl cytosine Embodiment 51. A composition comprising:
(a) one or more nucleic acid repair enzymes;
(b) a nucleotide mix comprising one or more modified nucleotides;
(c) a ligase; and
(d) a polymerase capable of nick translating activity.

Embodiment 52. The composition in embodiment 51, wherein the components of the composition are present in a single reaction vessel.

Embodiment 53. A method for detecting a damaged site in a double-stranded nucleic acid derived from a genomic nucleic acid, comprising:
(a) creating a nick at the damaged site;
(b) performing a nick translating reaction from the nick using a nucleotide mix comprising one or more modified nucleotides;
(c) sealing the nick-translated DNA in the double-stranded DNA with a ligase to form a double-stranded DNA product comprising a plurality of said modified nucleotides; and
(d) detecting the plurality of the modified nucleotides in the double-stranded DNA product, wherein said plurality of modified nucleotides correspond to the damaged site.

Embodiment 54. The method of any of preceding embodiments, wherein the double-stranded nucleic acid has at least one damaged nucleotide, and wherein step (a) comprises treating the double-stranded nucleic acid with one or more DNA repair enzymes to convert the damaged nucleotide to a nick.

Embodiment 55. The method of any of preceding embodiments, wherein the DNA polymerase used for nick translation and the ligase are contained in the same mixture.

Embodiment 56. The method of any of preceding embodiments, wherein detection step (d) comprises sequencing the product.

Embodiment 57. The method according to any of preceding embodiments, further comprising analyzing the sequence of the product to identify the location of the plurality of modified nucleotides and thereby identify the location of the nick.

Embodiment 58. The method according to any of preceding embodiments, further comprising prior to step (b) selecting a modified nucleotide capable of being differentiated from an unmodified nucleotide by a sequencing platform.

Embodiment 59. The method of any preceding embodiment, further comprising: enzymatically-treating or chemically-treating the product obtained in step (b) to change the identity of either the modified base or a corresponding unmodified base, but not both; sequencing the enzymatically-treated or chemically-treated product to produce a plurality of sequence reads; comparing the sequence reads to a reference sequence; and identifying the location of bases that have either changed or remained the same in the sequence reads, thereby identifying the location of the modified base.

Embodiment 60. The method of any preceding embodiment, wherein the modified dNTP comprises a 5-modified cytosine.

Embodiment 61. The method of any of preceding embodiment, wherein the 5-modified cytosine comprises 5-ca rboxylcytosine, 5-methylcytosine, 5-hydroxymethylcytosine, 5-formylcytosine, 5-bromocytosine, 5-propynylcytosine, 5-iodocytosine, 5-aminoallylcytosine, or 5-propargylaminocytosine.

EXAMPLES

Aspects of the present teachings can be further understood in light of the following examples, which should not be construed as limiting the scope of the present teachings in any way.
General Methods
Unless otherwise noted, all enzymes and reagents were from New England Biolabs, Ipswich, Mass.

Library Preparation and Sequencing for a Pacific Biosystems Platform

Libraries were prepared using the PacBio 2 kb Template Preparation and Sequencing Library Preparation protocol. In this protocol, DNA was treated with Exonuclease VII, FFPE DNA Repair Module (or an altered FFPE DNA Repair Module lacking T4 PDG for thymine dimer detection) and End Repair Module to repair and blunt-end all fragments. PacBio SMRTbell adapters were ligated to DNA fragments using T4 DNA ligase, followed by Exonuclease III and VII treatment to remove any unligated fragments. Unless stated otherwise, the modified nucleotides that were used for patch synthesis were $d^{6m}ATP$ and $d^{4m}CTP$ for Pac Bio sequencing, $d^{5m}CTP$ for Illumina and $d^{6m}ATP$ and detectable modified dCTP such as 5caC, 5mC, 5hmC, and/or 5fC for Oxford Nanopore sequencing.

The libraries were quantitated using Qubit® 3.0 Fluorometer (ThermoFisher Scientific, Waltham, Mass.) and sequenced on a PacBio RSII or Sequel instrument. Libraries sequenced on the RSII were sequenced using P6 Polymerase Chemistry, and Magnetic Bead loading for 360 minutes. Libraries sequences on the Sequel were sequenced using Polymerase 2.0 Chemistry, and diffusion loading for 600 minutes.

Reference Genomes

Three reference genomes were used in this study to map sequencing reads. For *T. kodakarensis* and *E. coli* MG1655 genomic libraries, the GenBank reference sequences AP006878.1 and NC_000913.3 were used, respectively. For *E. coli* ER1709 strain, a standard 20 kb PacBio library was created and sequenced on RSII instrument. The reference sequence was assembled using Hierarchical Genome Assembly Process (HGAP) for long single pass reads generated by PacBio SMRT sequencing. The resulting assembled reference sequence was deposited to GenBank with accession number CP030240.

Repair that Generates a Nick and Nick Translation

Repair enzymes and their canonical substrate(s) can be found in Table 1. For example, DNA is treated with Exonuclease VII, FFPE DNA Repair Module and End Repair Module to repair and blunt-end all fragments. Following nicking at DNA damage sites, the library was nick translated with Bst FL and a dNTP pool containing canonical and modified bases, followed by ligation with Taq DNA ligase and NAD+ or T4 DNA ligase.

SMRTbell adapters were then ligated on DNA fragments using T4 DNA ligase, followed by Exonuclease III and VII treatment to remove any unligated fragments to form a PacBio library. At least 500 ng of PacBio library was used in a 50 µl nick translation reaction. For nick translation, PacBio libraries were incubated with *Thermococcus* 9° N, RNase H2 (14) Bst FL DNA polymerase, and Taq Ligase (New England Biolabs, Ipswich, Mass.) (in excess), 1 µM NAD+, and 100 µM dGTP, dTTP, $d^{6m}ATP$ and $d^{4m}CTP$ (Trilink Biotechnologies, San Diego, Calif.) in 1× Detergent Free ThermoPol® buffer (New England Biolabs, Ipswich, Mass.) (20 mM Tris-HCl, 10 mM $(NH_4)_2SO_4$, 10 mM KCl, 2 mM $MgSO_4$, pH 8.8 at 25° C.) for 15 minutes, followed by AMPure® bead (Beckman Coulter, Brea, Calif.) clean-up. Bst FL DNA polymerase incorporates nucleotides 3' downstream of a nick site while subsequently removing downstream nucleotides (utilizing its 5' to 3' exonuclease activity), creating a patch of newly incorporated nucleotides with methylated A's and C's.

Nick translated libraries were treated with Exonuclease III and VII to remove any unligated nick sites, followed by 2× AMPure bead clean-up and quantitation by Qubit 3.0 Fluorometer. Total time for library construction was less than a day.

Data Analysis

Each nick translated library was sequenced in a single SMRT Cell using the PacBio RSII instrument with P6 Polymerase Chemistry, and Magnetic Bead loading for 360 minutes using PacBio Protocols.

Data analysis from PacBio sequencing data utilized three steps: (1) single-molecule modification detection, (2) identifying all continuous patches in single-molecule reads, (3) predicting nick-translation patches.

Sequencing data were mapped to the reference genome and 6 mA and 4mC incorporated by nick translation were reliably detected and distinguished from their unmodified counterparts by causing an increase in the sequencing polymerase IPD times during SMRT sequencing 14,15.

(1) Single-Molecule Modification Detection

All sequencing reads were mapped to a respective reference genome using the standard PacBio SMRT Analysis applications (RS_Resequencing) after filtering based on read length and quality followed by mapping reads to a reference genome using BLASR aligner (Pacific Biosystems)

Aligned subreads originating from a particular ZMW were extracted from the combined alignment and saved separately. PacBio modification detection tools were run on extracted subreads, and modification detection results (genomic position, strand, base, IPD ratio) were stored and analyzed. This procedure was repeated iteratively for subreads from each ZMW in the sequencing run.

(2) Identifying Continuous Patches in Single-Molecule Reads

For each single-molecule read, processed as described above, IPD ratios were examined at every position separately for each strand. The presence of modified bases 6 mA and 4mC was defined by observing IPD ratio >2.0 at positions occupied by A and C bases, respectively. Examining distributions of IPD ratios for 6 mA and 4mC showed that only 4% on non-modified A and C bases have IPD ratio greater than 2.0

At the same time, 95.8% of 6 mA's and 69.4% of 4mC's had IPD ratio greater than 2.0. The presence of multiple modified bases in a single-molecule read was used to define patches, which were defined as continuous read regions containing 6 mA's and 4mC's and were determined as follows. When a first A or C base with IPD ratio >2.0 was encountered, its position was recorded as the start of a patch. When the next modified A or C base was encountered, it was either used to extend the existing patch (and it was then recorded as the end of the patch in the current iteration), or it was used to start the new patch; other bases (G's and T's) were ignored. The procedure was repeated iteratively along the single-molecule read. There were two criteria to affect patch extension. Patches were expected to contain most of their A's and C's positions occupied by modified bases; however, some positions did not show high IPD ratio signal due to stochastic nature of polymerase kinetics. To account for such cases, the number of A's and C's with IPD ratio below cutoff was calculated between the previously defined patch end and the next encountered modified base. If four or less of such A's and C's were observed, the patch was extended; otherwise, the next encountered modified base started a new patch. Knowing the distribution of IPD ratios for 6 mA and 4mC, the probability of observing 4 modified bases with IPD ratio less than 2.0 was $(1-0.958)4=3.1\times10-6$ and $(1-0.694)4=6.8\times10-3$, respectively. The elimination of spurious readings had a negligible effect on the positive dataset. An additional rule prevented extending patches when the distance (i.e. number of A's, C's, G's and T's) between the previously defined patch end and the next encountered modified base was greater than 30. This was required in cases where single-molecule reads had an abundance of G's and T's with very few isolated A's and C's. Analysis of *T. kodakarensis* genome sequence showed that there was only a single location where the distance between A's or C's was greater than 30 bases.

(3) Predicting Nick-Translation Patches

Patches identified above included all continuous regions containing modified bases in all single-molecule sequencing reads. The length of the patch was in the range of 1 (a single isolated modified base) to N, where N is the maximum observed length of a single-molecule read (if the entire read comprised one long patch). Identified patches can originate from nick-translation or base modification detection noise. A classification model was developed to distinguish between nick translation patches and modification detection noise patches.

The patches that originated from nick-translation were longer and contained more modified bases, on average than those originating from base modification detection noise. The model was tested using the examples below.

Example 1: Determining Efficiency of Damage Detection of Genome Wide Ribonucleotide Substitution During normal genome replication in bacteria, yeast and archaea, DNA polymerases occasionally incorporate ribonucleotides due to the large excess of rNTPs compared to nucleotides in the cell (McElhinny, et al. Proc Natl Acad Sci USA 107, 4949-4954 (2010); Yoa, et al. Proc Natl Acad Sci 110, 12942-12947 (2013); Heider, et al. J. Biol Chem 292, 8835-8845 (2017)). Once embedded in genomic DNA, ribonucleotide monophosphates (rNMPs) lead to strand breaks and genome instability due to the reactive 2'-hydroxyl group (Lipkin, et al. J Am Chem Soc 76, 2871-2872 (1965); Li, et al. J. Am. Chem. Soc. 121, 5364-5372 (1999)). Cells have evolved a ribonucleotide excision repair (RER) pathway that is responsible for recognizing and repairing ribonucleotides from the genome where the ribonucleotide is an example of a damaged nucleotide. RER is initiated by the enzyme RNaseH2, which cleaves 5' to a ribonucleotide leaving a nick within the DNA. The frequency and location of ribonucleotides have been previously determined in genomic DNA from wild-type Tko and a mutant strain lacking RNaseH2 (Tko ΔRNaseH2) (Heider, et al. J. Biol Chem 292, 8835-8845 (2017)). For the present example, wild type Tko served as a control while the mutant represented the sample in which dT, dG, dC and dAs were substituted with rU, rG, rC and rA that constituted damaged bases.

Strain Construction and Isolation of Genomic DNA for Detection of Ribonucleotide Substitution in ΔRNaseH2 Bacterial Genomes and for Detection of the Origin of Replication in PolI/ΔRNaseH2 Bacterial Genomes

*Thermococcus kodakarensis* ΔRNaseH2 and wild-type strains were constructed and grown as previously described (Heider et al. (2017)). *E. coli* MG1655 and ER1709 (New England Biolabs, Ipswich, Mass.) and the ΔRNaseH2 (DrnhB) strain was obtained from the *Coli* Genetic Stock Center. *E. coli* ΔRNaseH2 was incorporated into the appropriate ER1709 background by P1 transduction.

*E. coli* ER1709 PolI/I709G strain was constructed using NEBuilder® HiFi DNA Assembly Master Mix (New England Biolabs, Ipswich, Mass.) with the amino acid change I709G into pDEL vector. Resulting plasmids were transformed into EC100D pir+(Lucigen). The PolI/I709G pDEL construct was integrated into *E. coli* ER1709 following the method of Tikh and Samuelson (Tikh, et al. Biology Methods and Protocols 1, bpw004 (2016)).

Following PolI/I709G mutant construction, the double ΔRNaseH2/PolI/I709G strain was generated by P1 transduction. Genomic DNAs were purified using the Qiagen Puregene® Kit B (Qiagen, Germantown, Md.) following the protocol for Gram-negative bacteria. Purified genomic DNA was quantified using Qubit 3.0 Fluorometer.

Ribonucleotide Detection

Genomic DNA purified from Tko and Tko ΔRNaseH2 organisms (5 µg) was sheared into 1 kb or 2 kb fragments by sonication (Covaris® 220 (Covaris, Woburn, Mass.)). Libraries were created directly from unamplified genomic DNA, preserving DNA damage originally present in the sample. Next, lesion-specific nicks were created within the library by incubating with DNA glycosylases and/or endonucleases (DNA repair enzymes) that recognized a damaged nucleotide (here a ribonucleotide) to generate a 3'-OH at the nick as described under "general methods". The DNA was sequenced and patches identified that contained modified nucleotides. The modified nucleotides were $d^{6m}ATP$ and $d^{4m}CTP$.

These patches marked regions of incorporated ribonucleotides, as shown in FIG. 4A-4D. The frequency and location of patches were correlated to ribonucleotide positions. From this data, it was observed that ribonucleotides were distributed across the genome. A 30-fold increase in genomic ribonucleotides were identified in the genome of Tko ΔRNaseH2 strains compared to parental wild-type Tko.

TABLE 6

Number of ribonucleotides detected from patch analysis in *T. kodakarensis* and *E. coli* genomic DNA.

| Organism | Total bases | Coverage | Ribonucleotides (per MB) | Ribonucleotides (per genome) | Organism |
|---|---|---|---|---|---|
| *T. kodakarensis* WT | 125,672,830 | 30.1 ± 2.4 | 11.0 ± 1.9 | 46 ± 8 | 3 |
|  |  | 11.0 ± 1.9 | 46 ± 8 3 |  |  |
|  |  | 46 ± 8 3 |  |  |  |
| *T. kodakarensis* ΔRNaseH2 | 63,074,699 | 15.1 ± 3.6 | 537.8 ± 2.2 | 2246 ± 9 | 3 |
| *E. coli* WT | 158,527,168 | 17.3 ± 10.1 | 2.3 ± 0.3 | 21 ± 3 | 2 |
| *E. coli* ΔRNaseH2 | 320,668,424 | 35.0 ± 4.0 | 20.6 ± 1.6 | 189 ± 15 | 3 |
| *E. coli* ΔRNaseH2/PolI SG | 1,690,807,200 | 184.5 ± 6.3 | 45.9 ± 1.4 | 421 ± 13 | 3 |

Individual sequencing runs were combined for data analysis. Standard deviations were determined from individual experimental replicates. Libraries were sequenced on RSII or SEQuel® instrument (PacBio, Menlo Park, Calif.). Ribonucleotide frequency was calculated per 10 Kb genomic intervals and for 95% of genomic intervals. For *T. kodakarensis*, the ribonucleotide frequency ranged from 371 to 706 ribonucleotides (per Mb) and the median ribonucleotide frequency was 538.6 (per Mb). For *E. coli*, the ribonucleotide frequency ranged from 6 to 39 ribonucleotides (per Mb) with a median ribonucleotide frequency of 20 (per Mb).

Example 2: Tracking In Vivo DNA Replication by Mapping Ribonucleotide Substitutions in a Cell with a Mutant PolI as Well as a Deletion of RNase H2

DNA replication in *E. coli* was tracked using the frequency and location of ribonucleotide insertions in the genome of *E. coli* ΔRNaseH2/PolI I709G. PolI performs Okazaki fragment maturation, and therefore predominately synthesizes DNA on the lagging strand. Importantly, both leading and lagging strand synthesis initiate near the oriC in *E. coli*. The incorporation of the I709G mutation within the PolI active site increases the efficiency of erroneous ribonucleotide incorporation and allows the correlation of ribonucleotide location and frequency to regions of PolI synthesis. In addition, the absence of RNaseH2 ensures ribonucleotides are retained in the genome.

Using methods for library construction and sequencing described above, a 2.2-fold increase in overall ribonucleotide frequency was observed in *E. coli* ΔRNaseH2/PolI I709G compared to *E. coli* ΔRNaseH2, confirming the PolI I709G mutation increased overall ribonucleotide incorporation efficiency. Furthermore, in the region surrounding oriC, we observed a characteristic transition in high ribonucleotide frequency from the top strand to the bottom strand, which represents the location where DNA replication initiates (FIG. 9A-9D). Mapping the frequency of ribonucleotides on the top strand defines the transition point, which occurs near the oriC (vertical line) (FIG. 9C-9D). To obtain the replication initiation start site, we determined the genomic location of the transition point as described above. The determined transition point occurs 53 bp to the left of oriC, which agrees with previous gel-based methods that track the location of RNA primers generated during lagging strand synthesis (Kohara, et al (1985) and Fang, et al. (1999)). Tracking ribonucleotide incorporation by a lagging strand DNA polymerase highlights the ability to predict DNA replication start points and more generally origins of replication (Gao, et al. Bioinformatics 23, 1866-1867 (2007)).

Example 3: Genome Wide 8-Oxo-dG Detection with Pacific Biosciences Sequencer $H_2O_2$ oxidizes DNA and increases frequency of 8-oxo-dG lesions in DNA (18). *E. coli* strain MG1655 cells were incubated with $H_2O$ or $H_2O_2$ (10 mM final concentration) for 15 minutes at 37° C. and genomic DNA was extracted. PacBio libraries from extracted genomic DNA were described above. At least 500 ng of PacBio library was used in a 50 µl nick translation reaction. For nick translation, PacBio libraries were first incubated with Fpg at 37° C. for 20 minutes. Nick translation only occurs at 8-oxo-dG sites cleaved by Fpg. Nick translation was completed by adding Bst FL, Taq Ligase (in excess), 1 µM NAD+, and 100 µM dGTP, dTTP, $d^{6m}$ATP and $d^{4m}$CTP in 1×Detergent Free ThermoPol buffer (20 mM Tris-HCl, 10 mM $(NH_4)_2SO_4$, 10 mM KCl, 2 mM $MgSO_4$, pH 8.8 @ 25° C.) for 20 minutes at 55° C., followed by AMPure bead clean-up. Nick translated libraries were cleaned up and sequenced as above.

Sequencing data were mapped to the reference genome and a detection algorithm (see FIG. 2) identified patches of $d^{6m}$ATP and $d^{4m}$CTP. These patches marked regions of 8-oxo-dG DNA damage. The frequency and location of patches correlated to 8-oxo-dG positions. From this data, it was observed that 8-oxo-dGs were distributed across the genome as shown in FIG. 7. A 4-fold increase in genomic 8-oxo-dGs were observed in in $H_2O_2$-treated strains compared to untreated control.

Example 4: Genome Wide DNA Damage Induced by a Site Specific Nicking Enzyme and Detection with Illumina Sequencing Using the method described below, DNA was nicked at a specific DNA sequence. Nick translation with modified dCTP created a patch of modified DNA that is resistant to deaminase or bisulfite treatment. Deaminase or bisulfite treatment converted all unmodified dCs in the genome to uracils except at patches of modified dC. Deaminase or bisulfite treated DNA was sequenced and mapped using Illumina sequencing and patches of dC corresponded to the site and strand of DNA damage in the genome.

In a 200 µl reaction, *E. coli* B strain genomic DNA (1 µg) was incubated with Nt. BstNBI (New England Biolabs, Ipswich, Mass.) in 1× NEBuffer 3.1 (New England Biolabs, Ipswich, Mass.) to create nicks at enzyme recognition sites. Following nicked DNA clean-up, nicked DNA (50 ng), in a 50 uL reaction, was incubated in 1× ThermoPol Buffer (20 mM Tris-HCl, 10 mM $(NH_4)_2SO_4$, 10 mM KCl, 2 mM $MgSO_4$, 0.1% Triton® X-100, pH 8.8@25° C.) with NAD+ (0.5 mM final concentration), dATP (0.2 mM), dGTP (0.2 mM), dTTP (0.2 mM), modified dCTP (e.g., a modified dCTP listed in Table 4) (0.2 mM), Bst FL (and Taq DNA ligase (in excess) for 30 minutes. T4βglucosyltransferase (T4-BGT) and uridine diphosphate glucose (40 µM final concentration) was added to the reaction and incubated for an additional 30 minutes. The reaction was cleaned up using AMPure beads (1×volume), washed twice with 80% ethanol and eluted DNA with 50 µl of TE (10 mM Tris, pH 8.0, 0.1 mM EDTA).

The treated DNA was used to create a DNA library for Illumina DNA sequencing as follows. The DNA was fragmented using the Covaris S2 and sheared DNA was prepared by NEBNext® Ultra™ II sample preparation according to published protocols (New England Biolabs, Ipswich, Mass.).

Next, the DNA library was deaminated to convert unmodified dC to uracil while patches of modified dC were not deaminated. Deamination can be completed by either bisulfite treatment (19) or APOBEC treatment as described below. Deamination was carried out by mixing denatured DNA (11.2 µl), BSA, RNase A, 1× reaction buffer (50 mM Bis Tris, pH 6.0, 0.1% Triton X-100), deaminase (0.004 mg/ml final concentration) and incubated for 3 hours. Next, the reaction was cleaned up using AMPure beads (1× volume), washed twice with 80% ethanol, and eluted with 23 µl 0.1×TE.

The deaminated DNA library was PCR amplified using NEBNext Universal PCR Primer for Illumina, NEBNext Index PCR Primer for Illumina and NEBNext Q5® Uracil PCR Master Mix (1×) (all commercially available from New England Biolabs, Ipswich, Mass.). DNA libraries were sequenced using the Illumina MiSeq® (Illumina, San Diego, Calif.) and sequencing reads mapped to a reference genome. The location and strand of cytosine patches remaining after deamination corresponded to the original location of the DNA nick. FIG. 5 shows that in deaminated genomic DNA, most cytosines are converted to uracils (grey) while a region of non-converted dC (black) is from a patch of nick translation using modified nucleotides as follows.

Example 5: Genome Wide DNA Damage Induced by a Site Specific Nicking Enzyme and Detection with PacBio Sequencing PacBio libraries were constructed from genomic DNA, nicked with Nb.BsrDI (The site-specific endonuclease Nb.BsrDI nicks one strand in duplex DNA at a defined DNA sequence (5'-NN|CATTGC-3') and therefore provides exact locations of nicks in DNA). Nicked genomic DNA was nick-translated to create patches of modified bases. Libraries were sequenced using SMRT sequencing on an RSII sequencer and single-molecule reads were mapped to a reference genome. Due to nick-translation, modified patches are expected to be present in close vicinity to Nb.BsrDI sites (on-target patches).

For nick translation, three replicate libraries for PacBio sequencing were generated by incubating genomic DNA with either Nb.BsrDI, Nb.BsmI, Nb.BssSI, or T4 PDG+Tth Endo IV, in NEB Buffer 3.1 for nicking under standard conditions and Bst FL, Taq Ligase, 1 µM NAD+, and 100 µM d6mATP (Trilink Biotechnologies), d4mCTP (Trilink Biotechnologies), dGTP and dTTP, 1× Detergent Free ThermoPol buffer (20 mM Tris-HCl, 10 mM (NH4)2SO4, 10 mM KCl, 2 mM MgSO4, pH 8.8 at 25° C.) for nick translation.

In this example, the location of the nicking site was known in advance to validate patches originating from nick-translation in close vicinity of the known nicking sites. Alternatively, any patches located far from known nicking sites would be evidence of base modification detection noise.

Any patch that started within 30 bases from any known nicking site, was defined as on-target. Any patch that started further than 500 bases away from any known nicking site was defined as off-target. In all three independent T. kodakarensis genomic libraries 4,881 on-target patches and 15,144 off-target patches with 5 or more modified bases were identified. Each patch, on-target or off-target, had several features associated with it: (1) patch length, (2) number of A's with IPD ratio >2.0, (3) number of C's with IPD ration >2.0, (4) total number of A's and C's with IPD ratio >2.0, (5) total number of A's, (6) total number of C's, (7) total number of A's and C's, (8) average IPD ratio for A's, (9) average IPD ratio for C's, (10) average IPD ratio for A's and C's, and fraction of modified bases, which is the number of A's and C's with IPD ratio >2.0 divided by total number of A's and C's (Schreiber, et al. Proc Natl Acad Sci USA 110, 18910-18915 (2013)). The results are shown in Table 7 and in FIG. 6A-6C.

The SVM model was separately trained on each of three independent T. kodakarensis experimental replicates at a time. This resulted in 4,174 on-target (true positive) and 14,911 off-target (true negative) patches correctly classified; 233 of on target (false negative) and 167 off-target (false positive) patches were misclassified. Therefore, the SVM model was able to correctly detect 96.6% of on-target patches (recall (accuracy); defined as tp/(tp+fn) fn=false negative). At the same time, 95.3% of all predicted patches were on-target patches (precision; defined as tp/(tp+fp) where tp=true positive and fp=false positive). The average recall and precision were 96.0±1.3% and 94.5±2.8%, respectively (see Table 7). The combined SVM model trained on T. kodakarensis data was also validated to predict patches in E. coli genomic DNA nicked with Nb.BsrDI followed by nick translation protocol. Three independent E. coli genomic libraries were created, and the average recall and precision were 93.5±0.9% and 99.4±0.3%, respectively. Finally, E. coli genomic DNA was nicked with two different nicking enzymes, Nb.BsmI and Nb.BssSI, followed by nick-translation protocol. The combined SVM model showed similar accuracy indicating that the SVM model is generally applicable (see Table 7).

TABLE 7

Model performance for nicking endonucleases

| Organism | Nicking enzyme | Recall % | Precision % | Replicates |
|---|---|---|---|---|
| T. kodakarensis | Nb.BsmI | 96.0 ± 1.3 | 94.5 ± 2.8 | 3 |
| E. coli | Nb.BsmI | 93.5 ± 0.9 | 99.4 ± 0.3 | 3 |
| E. coli | Nb.BsmI | 96.2 | 97.3 | 1 |
| E. coli | Nb.BsmI | 97.4 | 92.6 | 1 |

Example 6: Determining Efficiency of Damage Detection of Genome Wide UV Radiation Damage Genomic DNA Damage Assays For UV-radiation damage studies, 16 µg of purified E. coli MG1655 genomic DNA was exposed to UV-light using a Spectrolinker™ XL-1000 (Thomas Scientific, Swedesboro, N.J.) with the intensity setting (average ~2000 µwatt/cm2) for 10 seconds. Libraries were prepared and DNA sequenced as described above.

Patches detected using the above method of analysis revealed 911.5 thymine dimers per million bases, or 8,462 per E. coli genome. In addition, due to the extremely low background signal (<1.5 events in 1 million bases), rare DNA damage events were detected that could not be observed by previous DNA damage detection.

TABLE 8

Number of thymine dimers detected in E. coli genomic DNA exposed to UV radiation

| Exposure time (s) | Total bases | Coverage | Thymine dimers per Mb | Thymine dimers (per genome) | Replicates |
|---|---|---|---|---|---|
| 0 | 637,104,228 | 68.6 ± 5.7 | 2.8 ± 0.4 | 26 ± 4 | 4 |
| 5 | 122,423,747 | 13.2 ± 2.2 | 580.7 ± 26.8 | 5391 ± 249 | 4 |
| 10 | 86,614,891 | 9.3 ± 1.1 | 911.5 ± 25.2 | 8462 ± 234 | 4 |
| 20 | 22,463,093 | 2.4 ± 0.6 | 1275.6 ± 15.3 | 11842 ± 142 | 3 |

TABLE 8-continued

Number of thymine dimers detected in *E. coli* genomic DNA exposed to UV radiation

| Exposure time (s) | Total bases | Coverage | Thymine dimers per Mb | Thymine dimers (per genome) | Replicates |
|---|---|---|---|---|---|
| 30 | 5,442,312 | 0.6 ± 0.1 | 1532.4 ± 57.8 | 14226 ± 537 | 4 |
| 40 | 1,940,271 | 0.2 ± 0.1 | 1837.9 ± 60.8 | 17062 ± 564 | 4 |

Example 7: Genome Wide DNA Damage Detection of Stochastic Damage with a Nanopore Sequencer Nanopore sequencing is capable of sequencing very long DNA molecules (>30 kb). The following protocol outlines the replacement of damaged DNA with patches of modified nucleotides followed by detection and localization of the damage by Nanopore sequencing.

High molecular weight genomic DNA from an organism is purified using standard genomic DNA purification methods. DNA (1 to 1.5 μg in 45 μl TE) is then end repaired in a 60 μl reaction by mixing NEBNext Ultra II End Prep Enzyme Mix (3 μl) and NEBNext Ultra II End Prep Reaction Buffer (7 μl) and incubating at 20° C. for 30 minutes and followed by 65° C. for 30 minutes. Oxford Nanopore adaptor is ligated to the end prepped DNA by mixing DNA (30 μl) with adaptor mix (20 μl), and Blunt/TA Ligation Master Mix (50 μl) and incubated at 20° C. for 10 minutes. Damaged DNA is converted to a patch of modified nucleotides.

Damaged DNA can be cleaved with a corresponding DNA repair glycosylase and AP endonuclease (e.g., an enzyme from Table 1) to create a nick or 1 nt gap at the site of the lesion. The resulting nick (or 1 nt gap) is extended with Bst FL, Taq DNA ligase (in excess), NAD+, and modified nucleotide mix to replace a DNA lesion with a patch of modified bases detectable on the Oxford Nanopore. The modified nucleotide mix includes dGTP, dTTP, modified dATP ($d^{6m}ATP$) and detectable modified dCTP (such as 5caC, 5mC, 5hmC, and/or 5fC (20); see, e.g., Tables 4 and 5). Oxford Nanopore sequencing can detect the patch of modified nucleotides and thus identifies the sequence and the location of DNA damage (see Table 9).

Determining Replication Initiation Point Start Site

In the region surrounding the origin of replication, there is a characteristic transition in high ribonucleotide frequency from the top strand to the bottom strand. To precisely map the exact genomic location of the transition point, we calculated differential D" at each genomic location i according to the following equation: $D"=abs(RF(i-w, i)-RF(i, i+w))$, where i is a particular genomic location, RF(i−w, i) is the fraction of ribonucleotides on the top strand in (i−w, i) genomic interval, RF(i, i+w) is the fraction of ribonucleotides on the top strand in (i, i+w) genomic interval, w is the length of genomic interval. The genomic location, at which the differential achieves its maximal value, corresponds to the predicted initiation start site of replication. This location corresponds to the transition in high ribonucleotide frequency from the top strand to the bottom strand. The length of the genomic interval w was chosen to be 5,000 bases. In the *E. coli* ER1709 reference genome the transition point corresponds to position 1,486,629. A previously determined *E. coli* oriC sequence (378 nt) mapped to the region from position 1,486,682 to position 1,487,059. Thus, the predicted transition point is 53 bp to the left of the oriC sequence.

TABLE 9

Number of stochastic nicks detected in *T. kodakarensis* and *E. coli* genomic DNA

| Organism | Total bases | Coverage | Stochastic nicks per Mb | Stochastic nicks per genome | Replicates |
|---|---|---|---|---|---|
| *T. kodakarensis* | 303,300,443 | 72.6 ± 17.5 | 1.5 ± 0.3 | 6 ± 1 | 3 |
| *E. coli* | 369,627,873 | 39.8 ± 2.2 | 1.2 ± 1.3 | 11 ± 12 | 3 |

Individual sequencing runs were combined for data analysis. Standard deviations were determined from individual experimental replicates. Nicking enzyme was omitted from nick translation reaction. All libraries were sequenced on PacBio RSII instrument.

Although the foregoing embodiments have been described in some detail by way of illustration and example for purposes of clarity of understanding, it is readily apparent to those of ordinary skill in the art in light of the above teachings that certain changes and modifications can be made thereto without departing from the spirit or scope of the appended claims.

What is claimed is:

1. A method comprising:
nick translating a double-stranded nucleic acid comprising a nick in a reaction mix that comprises:
one or a plurality of enzymes that provide nick translating activity, a nucleotide mix comprising at least one modified nucleotide and a ligase,
wherein nick translation is initiated at the nick, a plurality of the at least one modified nucleotide is incorporated at or adjacent to the nick during nick translation and the ligase seals the nick translated nucleic acid,
wherein the at least one modified nucleotide is not fluorescent or biotinylated and/or the method involves sequencing the nick translated nucleic acid.

2. The method of claim 1, further comprises creating the nick by treating a double-stranded nucleic acid that has at least one damaged or mismatched nucleotide with one or more nucleic acid repair enzymes to convert the damage or mismatched nucleotide to a nick.

3. The method according to claim 2, further comprising determining the identity of the damaged or mismatched nucleotide based on the selection of nucleic acid repair enzyme.

4. The method according to claim 2, wherein the one or more nucleic acid repair enzymes are selected from the group consisting of: APE 1, Endo III, Endo IV, Endo V, Endo VIII, Fpg, hOGG1, hNEIL1, T7 Endo I, T4 PDG, UDG, hSMUG1 and hAAG.

5. The method of claim 1, further comprising sequencing the nick translated nucleic acid.

6. The method of claim 5, further comprising identifying a patch of sequence that comprises a plurality of the at least one modified nucleotides.

7. The method according to claim 6, identifying the location of the nick by analyzing the location of the patch from the sequence that comprises the plurality of the at least one modified nucleotide.

8. The method according to claim 1, further comprising selecting one or more modified nucleotides capable of being differentiated from the corresponding unmodified nucleotide by a sequencing platform.

9. The method according to claim 1, wherein the modified nucleotide has a modified base, the method further comprising:
(a) enzymatically-treating or chemically-treating the nick translated nucleic acid to change the identity of either the modified base or a corresponding unmodified base, but not both;
(b) sequencing the enzymatically-treated or chemically-treated nucleic acid from (a) to produce a plurality of sequence reads;
(c) comparing the sequence reads to a reference sequence; and
(d) identifying the location of bases that have either changed or remained the same in the sequence reads, thereby identifying the location of the modified base.

10. The method according to claim 9, wherein the enzyme or chemical treatment is a sodium bisulfite treatment.

11. The method according to claim 9, wherein the enzyme or chemical treatment is a treatment with a DNA deaminase.

12. The method according to claim 9, further comprising detecting to a first degree of confidence the position and identity of a damaged nucleotide in the double-stranded nucleic acid.

13. The method according to claim 1, wherein the modified nucleotide is not fluorescent or biotinylated.

14. The method according to claim 1, wherein the nick translation is done using full length Bst DNA polymerase or DNA polymerase I.

15. The method according to claim 1, wherein the one or a plurality of enzymes that provide nick translating activity comprises a strand-displacing polymerase and a flap endonuclease.

16. The method according to claim 1, wherein the at least one modified nucleotide in the reaction mix does not comprise an optically-detectable moiety or an affinity tag.

17. The method according to claim 1, wherein the double-stranded nucleic acid is a genomic DNA or derived from genomic DNA.

18. The method according to claim 1, wherein the at least one modified nucleotide comprises a 5-modified cytosine.

19. The method according to claim 1, wherein the at least one modified nucleotide comprises 5-carboxylcytosine, 5-methylcytosine, 5-hydroxymethylcytosine, 5-formylcytosine, 5-bromocytosine, 5-propynylcytosine, 5-iodocytosine, 5-aminoallylcytosine and 5-propargylaminocytosine.

20. The method according to claim 1, wherein the nick is the product of a stochastic event.

21. The method according to claim 1, wherein the nick is the product of a non-stochastic event.

22. The method according to claim 1, further comprising detecting one or more stochastic events that result in nicks.

23. The method of claim 22, wherein the one or more stochastic events are detected by sequencing and wherein the method further comprises identifying patches containing one or more modified nucleotides resulting from nick translating the nucleic acid from a nick resulting from the stochastic event.

24. A composition comprising:
(a) one or more nucleic acid repair enzymes;
(b) a nucleotide mix comprising one or more modified nucleotides that are not fluorescent or biotinylated;
(c) a ligase; and
(d) a polymerase capable of nick translating activity.

25. The composition according to claim 24, wherein the components of the composition are present in a single reaction vessel.

26. A method for detecting a damaged site in a double-stranded nucleic acid derived from a genomic nucleic acid, comprising:
- (a) creating a nick at the damaged site;
- (b) performing a nick translating reaction from the nick using a nucleotide mix comprising one or more modified nucleotides;
- (c) sealing the nick-translated DNA in the double-stranded DNA with a ligase to form a double-stranded DNA product comprising a plurality of said modified nucleotides; and
- (d) detecting the plurality of the modified nucleotides in the double-stranded DNA product, wherein said plurality of modified nucleotides correspond to the damaged site wherein the one or more modified nucleotides are not fluorescent or biotinylated and/or the method involves sequencing the nick translated nucleic acid.

27. The method according to claim 26, wherein the double-stranded nucleic acid has at least one damaged nucleotide, and wherein step (a) comprises treating the double-stranded nucleic acid with one or more DNA repair enzymes to convert the damaged nucleotide to a nick.

28. The method according to claim 26, wherein the nick translating reaction utilizes a DNA polymerase and where the DNA polymerase and the ligase are contained in the same mixture.

29. The method according to claim 26, wherein detection step (d) comprises sequencing the product.

30. The method according to claim 26, further comprising analyzing the sequence of the product to identify the location of the plurality of modified nucleotides and thereby identify the location of the nick.

31. The method according to claim 26, further comprising prior to step (b) selecting a modified nucleotide capable of being differentiated from an unmodified nucleotide by a sequencing platform.

32. The method according to claim 26, further comprising:
- enzymatically-treating or chemically-treating the product obtained in step (b) to change the identity of either the modified base or a corresponding unmodified base, but not both;
- sequencing the enzymatically-treated or chemically-treated product to produce a plurality of sequence reads;
- comparing the sequence reads to a reference sequence; and
- identifying the location of bases that have either changed or remained the same in the sequence reads, thereby identifying the location of the modified base.

33. The method according to claim 26, wherein the one or more modified nucleotide comprises a 5-modified cytosine.

34. The method according to claim 33, wherein the 5-modified cytosine is selected from the group consisting of 5-carboxylcytosine, 5-methylcytosine, 5-hydroxymethylcytosine, 5-formylcytosine, 5-bromocytosine, 5-propynylcytosine, 5-iodocytosine, 5-aminoallylcytosine, and 5-propargylaminocytosine.

* * * * *